United States Patent
Inazawa et al.

(10) Patent No.: US 8,216,785 B2
(45) Date of Patent: Jul. 10, 2012

(54) METHOD FOR DETECTING NEUROBLASTOMA

(75) Inventors: Johji Inazawa, Tokyo (JP); Issei Imoto, Tokyo (JP); Jun Inoue, Tokyo (JP)

(73) Assignees: Fujifilm Corporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 297 days.

(21) Appl. No.: 12/568,569

(22) Filed: Sep. 28, 2009

(65) Prior Publication Data

US 2010/0105868 A1    Apr. 29, 2010

(30) Foreign Application Priority Data

Oct. 27, 2008 (JP) ................. 2008-275176

(51) Int. Cl.
*C12Q 1/68* (2006.01)
*G01N 33/53* (2006.01)

(52) U.S. Cl. ....................... 435/6.1; 435/7.1

(58) Field of Classification Search .................. None
See application file for complete search history.

(56) References Cited

OTHER PUBLICATIONS

Tockman et al (Cancer Res., 1992, 52:2711s-2718s).*
Brodeur, "Neuroblastoma: Biological Insights Into a Clinical Enigma", Nature Reviews,Cancer, vol. 3, Mar. 2003, pp. 203-216.
Westermann et al., "Genetic Parameters of Neuroblastomas", Cancer Letters, vol. 184, 2002, pp. 127-147.

* cited by examiner

*Primary Examiner* — Sean Aeder
(74) *Attorney, Agent, or Firm* — Birch, Stewart, Kolasch & Birch, LLP

(57) ABSTRACT

The present invention is intended to provide a means for judging the malignancy of neuroblastoma and the progress of spontaneous regression thereof. The present invention provides a method for detecting cancer which comprises detecting activation or inactivation of the lysosomal-associated protein multispanning transmembrane 5 (LAPTM5) gene and amplification of the MYCN gene in a specimens to evaluate the malignancy of the specimens and the progress of spontaneous regression.

4 Claims, 37 Drawing Sheets

SEQUENCE LISTING

```
<160> NUMBER OF SEQ ID NOS: 75

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 1
tggtagtgtt tttttagtaa gt                                              22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
aaaaattctt tcatttataa aaaa                                            24

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
gttaaatggt tgggggtatt ttg                                             23

<210> SEQ ID NO 4
<211> LENGTH: 22
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 4
aacttcacaa attacccaac aa                                                22

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
ttagttgttg ttaagat                                                      17

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
aaaaccctcc tccaaaacct a                                                 21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
tgtttcgttt tagttgtga                                                    19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
tgttttgttt tagttgtga                                                    19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
ttaaccacag gccctgagtc                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
gcttccagct cagtcaaacc                                            20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
cagagaggtg gagagcagga                                            20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
ccccttcagt gtctcagagg                                            20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
tagcaaaggg tcctgaagtt                                            20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gctcactgca agctccgcct                                            20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
agacagacgg gggcccccctt                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
ccacacatca tatgcaggtg                                         20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
cctccagtga gatgtgcatt                                         20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
tgcctggggt gtcctttcac                                         20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
tggcttctct cctccatcct                                         20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
gacccctggc tgcctctttc                                         20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gccaccaggg gctcacttgg                                         20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
agacgtctgg ctggccaggc                                         20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
acacaccaaa gcctgcctgg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gctgcagtga gcgatgagcc                                              20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
ccagacacac cccctcccac c                                            21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
tcccttaagc ccctcacctc                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
cagggccagg actcaggatt                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
ctgtgtccag tggggctagg                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
acaatgccca ccttctgggc                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
cgccaggaaa acggcgtgaa                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
gctcactgca agctccgctt                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
gcaggacgtg tctgcgcggg                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
ggtcgcacag ccaggcggca                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
acccagcccc ggccgggcct                                              20

<210> SEQ ID NO 35
<211> LENGTH: 20

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
aaccttaaca gccccacagt                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
cagatggggc ctgcggtgac                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
gggtgggcca agcaagggct                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
gtcttgggca agtcacagtg                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
gcagaggggc agccttggcc                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
ccatgtggtg agtgtgcggg                                              20

<210> SEQ ID NO 41
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 41
caagaggccc aggacaccat                                                 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
tggtgttgca gcccggaacc                                                 20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
gctcactgca agctccacct                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
gggcttgaga tcccgagagg                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
gtccctgcaa atcatggact                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
aggtgggcac ttccatgtag                                                 20

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued

DNA

<400> SEQUENCE: 47
ccgtgctagc tcctccaagt tcc                                           23

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
ctaccggaag cactttctcg                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
cacacaccaa ctttgccatc                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
aactcatttg tgggcctgac                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
ttgagcatcc tgctgttgtc                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
ttcaggcagc agtgttcatc                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 53
taaaccaagc aaccctggac                                           20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
aagcacaatc acctgctcct                                           20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
gtccgtgttg acctgatcct                                           20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
gtccctgcaa atcatggact                                           20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
aggtgggcac ttccatgtag                                           20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58
atcgagaagc tgtccaggaa                                           20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
```
ggatccgtca atgaggaaga                      20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
cctcagtttc ttcatctgta                      20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
ccaggactgt taccaagccc                      20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
cttccaaagt tggtagtgtt                      20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
cctgcccctt agacaggcag                      20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
aaggaagtga ggagggcagc                      20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 65
ttcacactca cacaagcacg                      20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
tgtctgcggt gacccgtcat                                            20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 67
acagaggcag aaacggagcc                                            20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
gtgaggtcgg ccgcagacac                                            20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
ccagtgacag ccgtgacttc                                            20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
agcctttgtg cggttcgtg                                             19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
cccccgtgac ctttaccctg                                            20

<210> SEQ ID NO 72

```
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
ccgctcgaga tggaccccccg cttgtc                                          26

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 73
ccggaattct cacacctctg agtat                                            25

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
atggaccccc gcttgtccac                                                  20

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
tcacacctct gagtatggg                                                   19
```

METHOD FOR DETECTING NEUROBLASTOMA

TECHNICAL FIELD

The present invention relates to a method for detecting cancer and, in particular, neuroblastoma.

BACKGROUND ART

Neuroblastoma (NB) is a tumor that develops in the adrenal gland or sympathetic ganglia, and the neural crest-derived cell is considered to be a neuroblastoma-developing cell. The clinical behavior of neuroblastoma is known to be characteristic. In the case of favorable tumor that develops in a person who is younger than 1 year old, programmed cell death (PCD) occurs and the tumor spontaneously disappears (i.e., spontaneous regression) without therapeutic intervention. Also, such favorable tumor differentiates and matures into favorable ganglioneuroma (GN). Unfavorable tumor, however, develops into advanced tumor, even if a potent chemotherapy is provided, which often results in death (Brodeur., et al., Nat Rev Cancer, 2003, 3, 203-216; and Westermann et al, Cancer Lett, 2002, 184, 127-147). In contrast, neuroblastoma that develops in a 1-year-old or older person is generally advanced, and a potent therapy composed of surgery, chemotherapy, and radiation therapy is necessary. When neuroblastoma is in stage 4 or the number of cancer genes (MYCN) is amplified, in particular, active therapy involving hematopoietic stem cell transplantation (e.g., bone marrow transplantation or peripheral blood stem cell transplantation) is performed. In the case of stage 4 neuroblastoma, however, the "5-year survival rate" is approximately 30%, even if the active therapy involving hematopoietic stem cell transplantation is performed. Accordingly, development of an effective method for detecting and treating neuroblastoma is awaited via discovery of a causative gene associated with neuroblastoma development and elucidation of functions of such gene.

Specifically, discovery of a causative gene for spontaneous regression of neuroblastoma, elucidation of the molecular mechanism thereof, and development of a novel method for detecting or diagnosing cancer based on such finding are desired. By detecting characteristics of the causative gene, an adequate therapy can be selected for a patient without performing useless therapy.

DISCLOSURE OF THE INVENTION

Elucidation of the molecular mechanism of spontaneous regression of neuroblastoma on a genetic level would enable evaluation of spontaneous regression of neuroblastoma via a genetic detection technique, diagnosis of malignancy, and suppression of advancement. Further, selection and development of a drug and establishment of a therapy method based on the mechanism would become possible. Specifically, a gene exhibiting a behavior that is characteristic of spontaneous regression of neuroblastoma is identified to perform gene-centered technical examination, so that evaluation of spontaneous regression of neuroblastoma, diagnosis of malignancy, and suppression of advancement can be performed. More specifically, the present invention is intended to provide a method of detecting cancer by identifying a gene exhibiting a behavior characteristic of spontaneous regression of neuroblastoma.

The bacterial artificial chromosome array-based methylated CpG island amplification (BAMCA) technique based on comparative genomic hybridization (CGH) is a simple, rapid, and effective method for searching for a methylated region in the genome (Toyota M. et al., Cancer Res, 2005, 10, 2307-2312, Inazawa J., et al., Cancer Sci, 2004, 95, 559-563, Misawa A. et al., Cancer Res, 2005, 65, 10233-10242, Sugino Y. et al., Oncogene, 2007, 26, 7401-7413, Tanaka K. et al, Oncogene, 26, 6456-6468). By this technique, the present inventors succeeded in identifying that a gene associated with spontaneous regression of neuroblastoma; i.e., the lysosomal-associated protein multispanning transmembrane 5 (LAPTM5) gene, would be inactivated via methylation in the case of neuroblastoma. As a result of subsequent detailed analysis, the molecular mechanism of spontaneous regression of neuroblastoma on a genetic level as indicated below was elucidated (FIG. 5f; FIG. 16).

Expression of LAPTM5 is suppressed via methylation in either favorable or unfavorable neuroblastoma. It was considered that when neuroblastoma reaches at a given programmed stage, LAPTM5 expression would be activated in tumor cells, the cells would differentiate or die, and the whole tumor would be regressed. LAPTM5 activation in such a case was considered to be affected by stress such as mitochondrial injury, a differentiation-inducing stimulus, demethylation, and MYCN expression suppression. In the case of unfavorable tumor that would not undergo regression, the LAPTM5 copy number frequently decreases and MYCN gene amplification frequently occur, in addition to methylation. Even if the above-described programmed event associated with LAPTM5 activation occurred, accordingly, cell differentiation and cell death were considered to be less likely to occur due to the lowered absolute expression level of LAPTM5.

In LAPTM5-induced cell death, further, accumulation of LAPTM5, in addition to activation of expression thereof, was considered to be deeply associated with induction of cell death. The accumulated LAPTM5 was considered to lead to lysosome instability, and LAPTM5 would be synergistically accumulated due to such lysosome instability. Consequently, lysosome instability leads to translocation of cathepsin to the cytoplasm and accumulation of ubiquitinated proteins upon blocking of an autophagy pathway, which would be lead to cell death. Such LAPTM5-mediated molecular mechanism was considered to cause spontaneous regression of neuroblastoma.

Thus, the present inventors identified that LAPTM5 was activated in the region where tumor degeneration that exhibits spontaneous regression of favorable tumor occurs based on immunohistological staining using the antibody specific to LAPTM5. Also, the present inventors succeeded in discovering that the increased LAPTM5 gene transcripts or proteins in the unfavorable neuroblastoma-derived cell lines would specifically lead to significantly lowered neuroblastoma growth and would induce cell death, thereby completing the present invention.

The present invention provides a method for detecting cancer which comprises detecting activation or inactivation of the lysosomal-associated protein multispanning transmembrane 5 (LAPTM5) gene and amplification of the MYCN gene in a specimens to evaluate the malignancy of the specimens and the progress of spontaneous regression.

Preferably, inactivation of the LAPTM5 gene is caused by methylation at the CpG site in the vicinity of the transcription initiation point, deletion of the LAPTM5 gene, or suppression of transcription by MYCN.

Preferably, inactivation of the LAPTM5 gene is detected by RT-PCR, real-time RT-PCR, FISH, array-CGH, MsSNuP, bisulfite sequencing, or COBRA.

The present invention further provides a method for detecting cancer which comprises detecting the amount of proteins translated from the lysosomal-associated protein multispanning transmembrane 5 (LAPTM5) gene and amplification of the MYCN gene in a specimens to evaluate the malignancy of the specimens and the progress of spontaneous regression.

Preferably, the amount of proteins translated from the LAPTM5 gene is detected by the immunohistochemical method.

Preferably, the specimens is neural crest-derived tissue.

Preferably, the cancer is neuroblastoma.

The present invention further provides a method for suppressing cell growth which comprises introducing the lysosomal-associated protein multispanning transmembrane 5 (LAPTM5) gene or a protein encoded by the LAPTM5 gene into a cell in vivo or in vitro.

The present invention further provides a suppressor for cell growth which comprises the lysosomal-associated protein multispanning transmembrane 5 (LAPTM5) gene or a protein encoded by the LAPTM5 gene.

The present invention enables accurate comprehension of canceration, malignancy, and spontaneous regression tendency in neural crest-derived cell specimens. Also, introduction of LAPTM5 gene transcripts in neuroblastoma enables suppression of neuroblastoma growth and induction of cell death.

BRIEF DESCRIPTION OF THE DRAWINGS

FIG. 1 shows the analysis of methylation and expression of the LAPTM5 gene in the neuroblastoma cell line and in the tumor.

FIG. 1(e) shows comparison of methylation frequency in neuroblastoma and GN. Typical results of bisulfite sequencing at CG sites in the vicinity of the transcription initiation site of LAPTM5 are shown. Methylation conditions are shown with a white (nonmethylated) or black (methylated) circle. An arrow indicates the transcription initiation site.

FIG. 2 shows LAPTM5 activation in the degenerating cell in the favorable tumor specimen and induction of cell death by forced LAPTM5 expression in the neuroblastoma cell line.

FIG. 3 shows generation of LMP and blocking of the autophagy pathway upon LAPTM5-induced cell death.

FIG. 5 shows induction of LAPTM5 expression via treatment with MPP+ or $H_2O_2$ and suppression of expression thereof by MYCN.

FIG. 6 shows searching for of the candidate gene, the expression of which is to be suppressed via methylation of DNA.

Frequency of 1p deletion from the neuroblastoma cell line was elucidated via array-CGH. With the use of MCG Cancer Array-800 comprising arbitrary BAC containing 43 BAC located in 1p spotted thereon, 10 neuroblastoma cell lines were analyzed. A horizontal red (4 non-MYCN-amplified neuroblastoma cell lines) or blue (the MYCN-amplified neuroblastoma cell line) bar represents frequency of deletion from BAC. Deletion of a large area from 1p comprising the LAPTM5 gene locus was frequently detected in the MYCN-amplified neuroblastoma cell line.

FIG. 8 shows the Ms-SNuPE analysis of methylation.

Figure 8A:
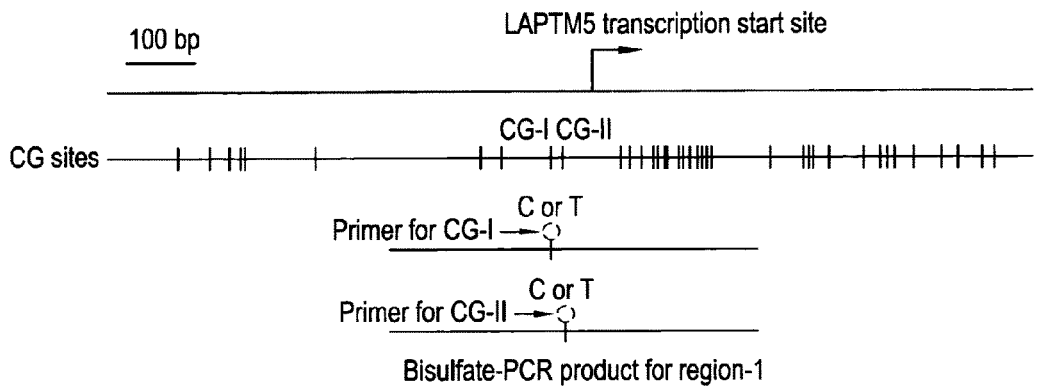

FIG. 8(a) shows positions of primers used for methylation-sensitive single-nucleotide primes extension (Ms-SNuPE) analysis. The bisulfite-PCR product of Region I was subjected to gel purification. Arrows indicate positions of primers used for the primer extension experiment. When the CG site is methylated or nonmethylated, C or T is added, respectively.

Figure 8B:
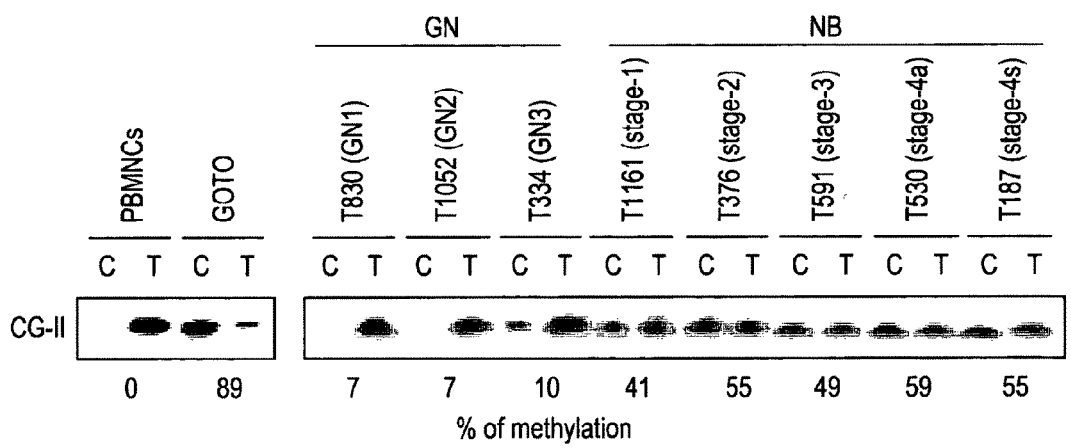

FIG. 8(b) shows a representative image of CG-II obtained via Ms-SNuPE analysis. The purified bisulfite-PCR product (25 ng), the primer, and radioisotope-labeled C or T were subjected to the reaction for primer extension. The product was electrophoresed via PAGE, following purification. The values of methylation of the CG sites were determined by the formula: methylated C/(methylated C+nonmethylated T)×100. The tumor sample numbers T830, T1052, and T334 reflect GN1, GN2, and GN3 in FIGS. 2b and 2c.

Figure 9:
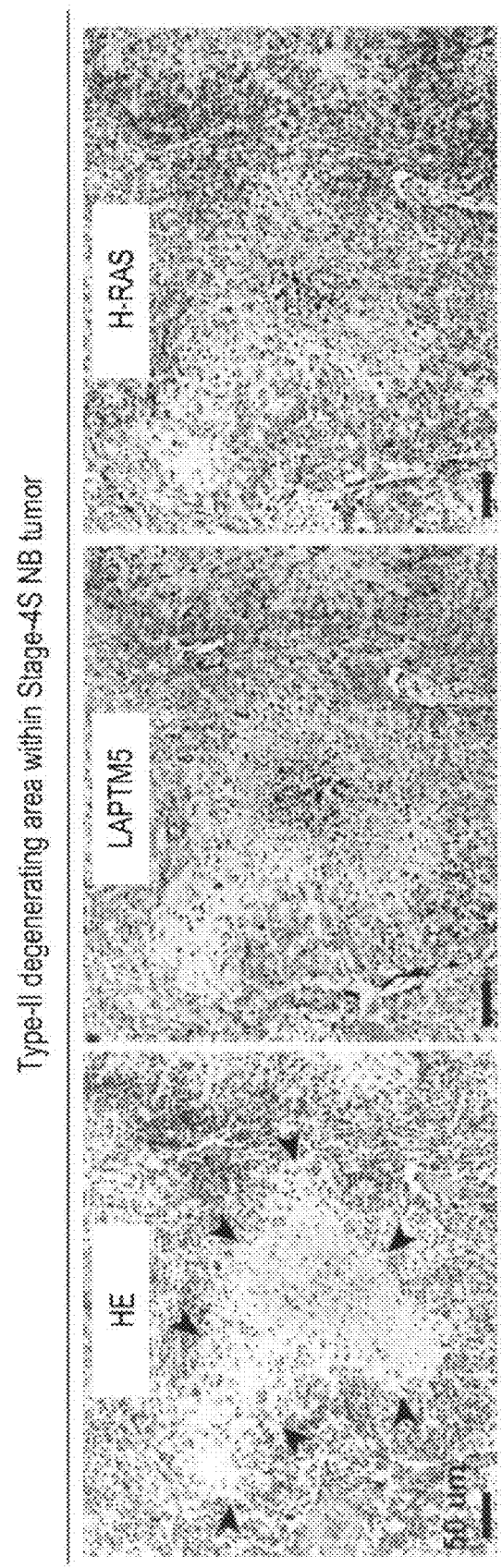

FIG. 9 shows representative images of tumor-degenerating range within neuroblastoma tumors in stage 4S obtained via immunochemical staining with LAPTM5 or H-ras. Representative images are obtained via staining with hematoxylin-eosin (HE) (left), the LAPTM5 antibody (center), and the H-ras antibody (right).

Figure 10A:
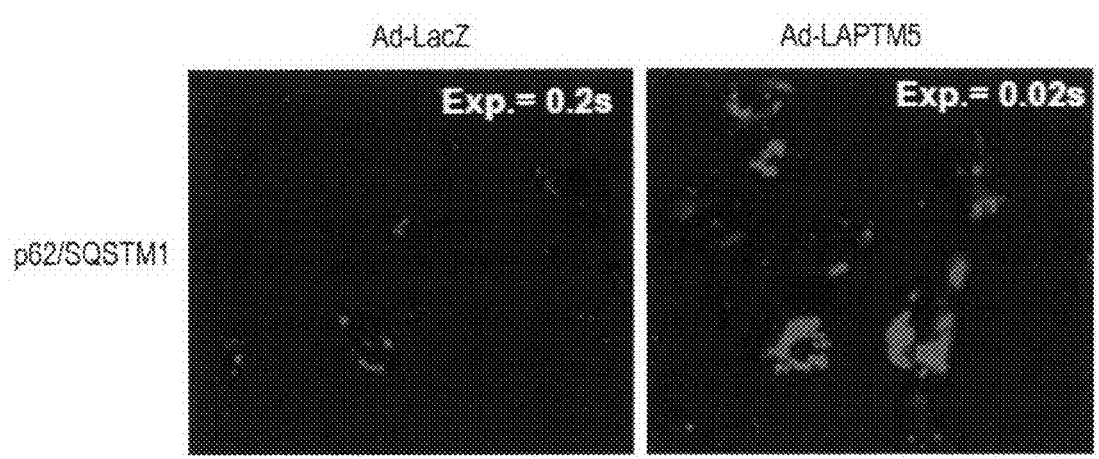
Figure 10B:
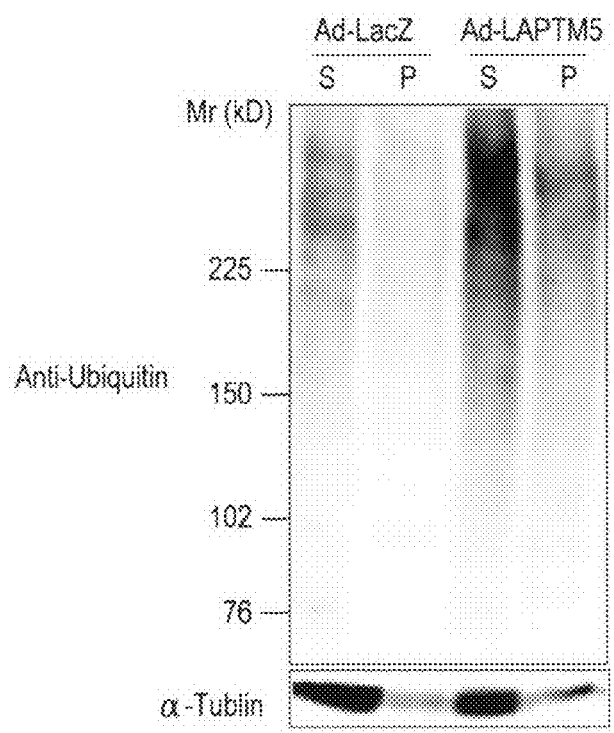

FIG. 10 shows accumulation of p62/SQSTM1 and ubiquitinated proteins in the GOTO cells infected with Ad-LacZ or Ad-APTM5.

Four days after infection, the cells were fixed, subjected to the immune reaction with the use of the p62/SQSTM1 antibody, and visualized with the use of the Texas Red complex secondary antibody. The cell extract was prepared with the use of 0.1% Triton Xn. Fractions that are insoluble in Triton X were dissolved in 2% SDS. Fractions that are soluble or insoluble in Triton X were separated via 6% SDS-PAGE and subjected to Western blot analysis with the use of relevant antibodies.

FIG. 11 shows lysosomal membrane permeabilization (LMP) upon LAPTM5-induced cell death.

Figure 11A:
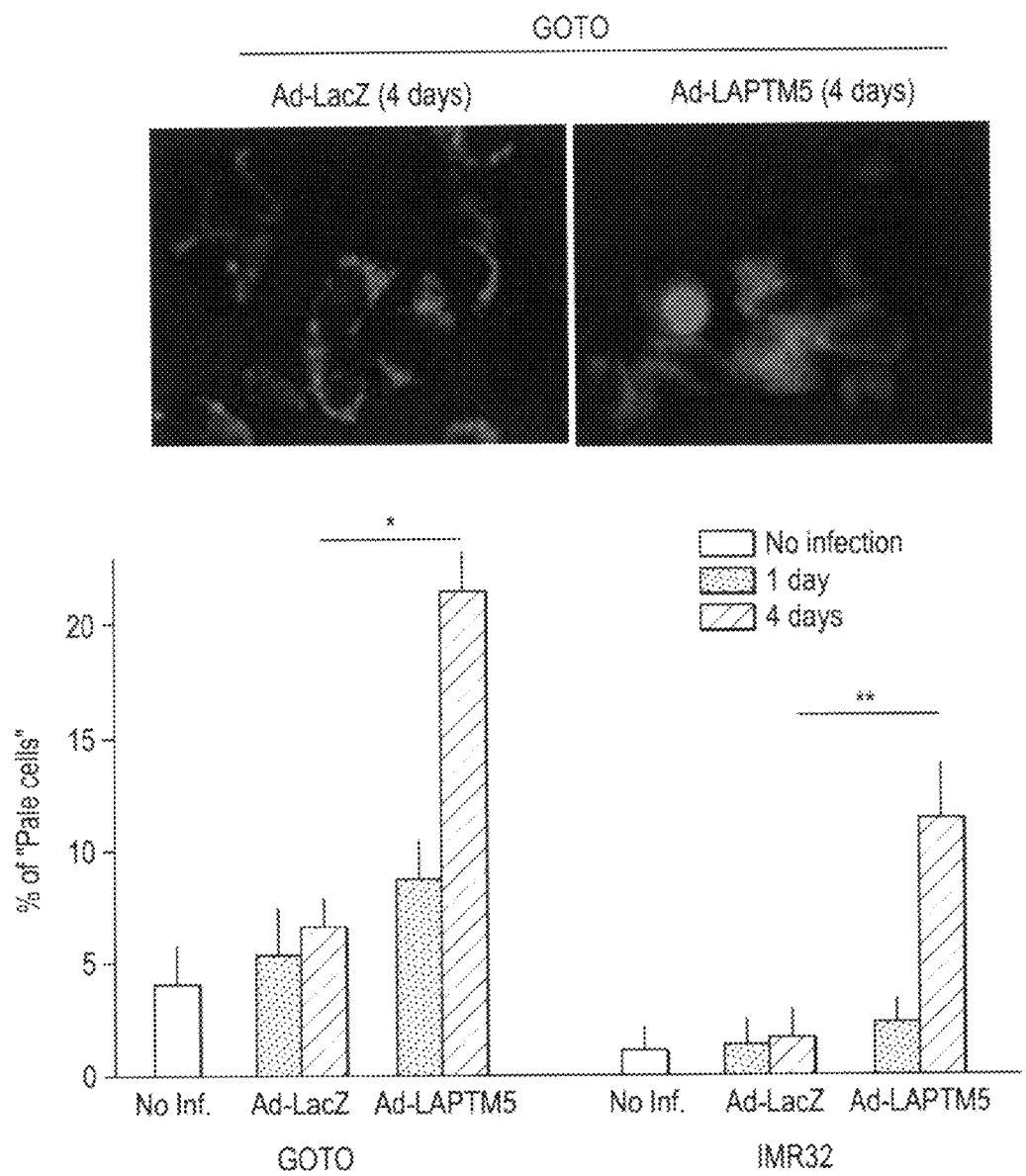

FIG. 11(a) shows frequency of cells exhibiting dot-like patterned deletion obtained via LTR staining. Frequency of cells exhibiting dot-like patterned deletion was determined 1 or 4 days after infection with Ad-LacZ or Ad-LAPTM5. The upper portion shows a typical image. The percentage relative to all cells was recorded. The figure shows the percentage of cells in both cell lines. A vertical line represents the standard deviation of 3 independent experiments (*P<0.001, **P<0.05). "No inf" represents an uninfected sample.

Figure 11B:
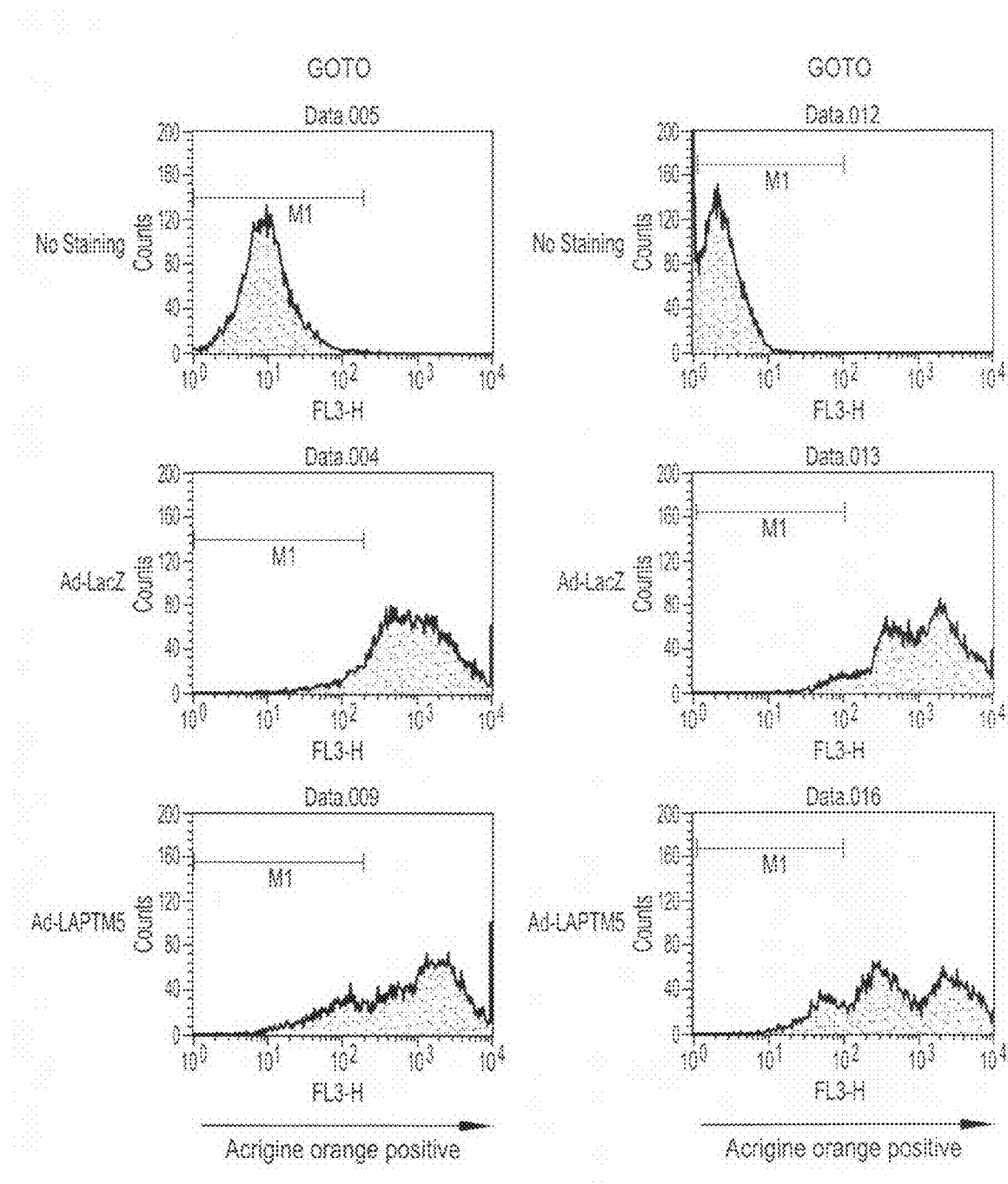

FIG. 11(b) shows an example of FACS analysis of infected GOTO cells and IMR cells via acridine orange (AO) staining.

Figure 11C:
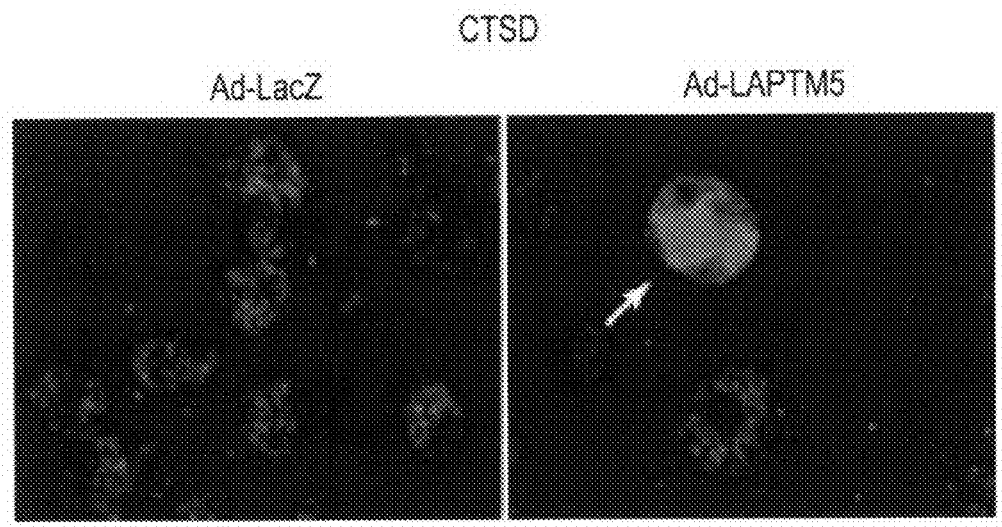

FIG. 11(c) shows release of cathepsin D (CTSD) from the lysosome to the cytoplasm. The figure shows CTSD protein localization. Four days after infection, cells were fixed, subjected to the immune reaction with the use of the CTSD antibody, and visualized with the use of the Texas Red complex secondary antibody. An arrow indicates a cell in which CTSD is released into the cytoplasm.

Figure 12:
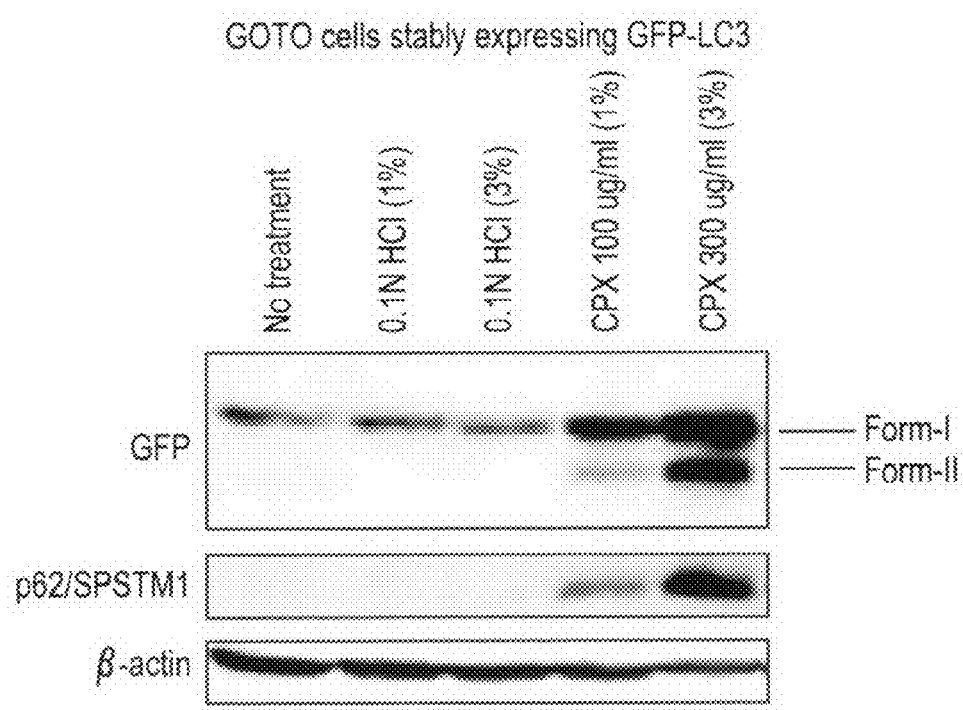

FIG. 12 shows detection of GFP-LC3 type II proteins via treatment with a LMP-inducing drug and accumulation of p62/SQSTM1 proteins.

The GOTO cells ($1\times10^6$ cells/well) that stably express GFP-LC3 were sowed on a 6-well plate and treated with ciprofloxican (CPX) (100 or 300 μg/ml) or a solvent thereof (0.1N hydrochloric acid) so as to induce LMP. The total cell extract obtained from the treated cells was electrophoresed via SDS-PAGE and subjected to immunoblot analysis using antibodies reacting with relevant proteins.

FIG. 13 shows activation of LAPTM5 expression along with induction of differentiation in vitro.

Figure 13A:
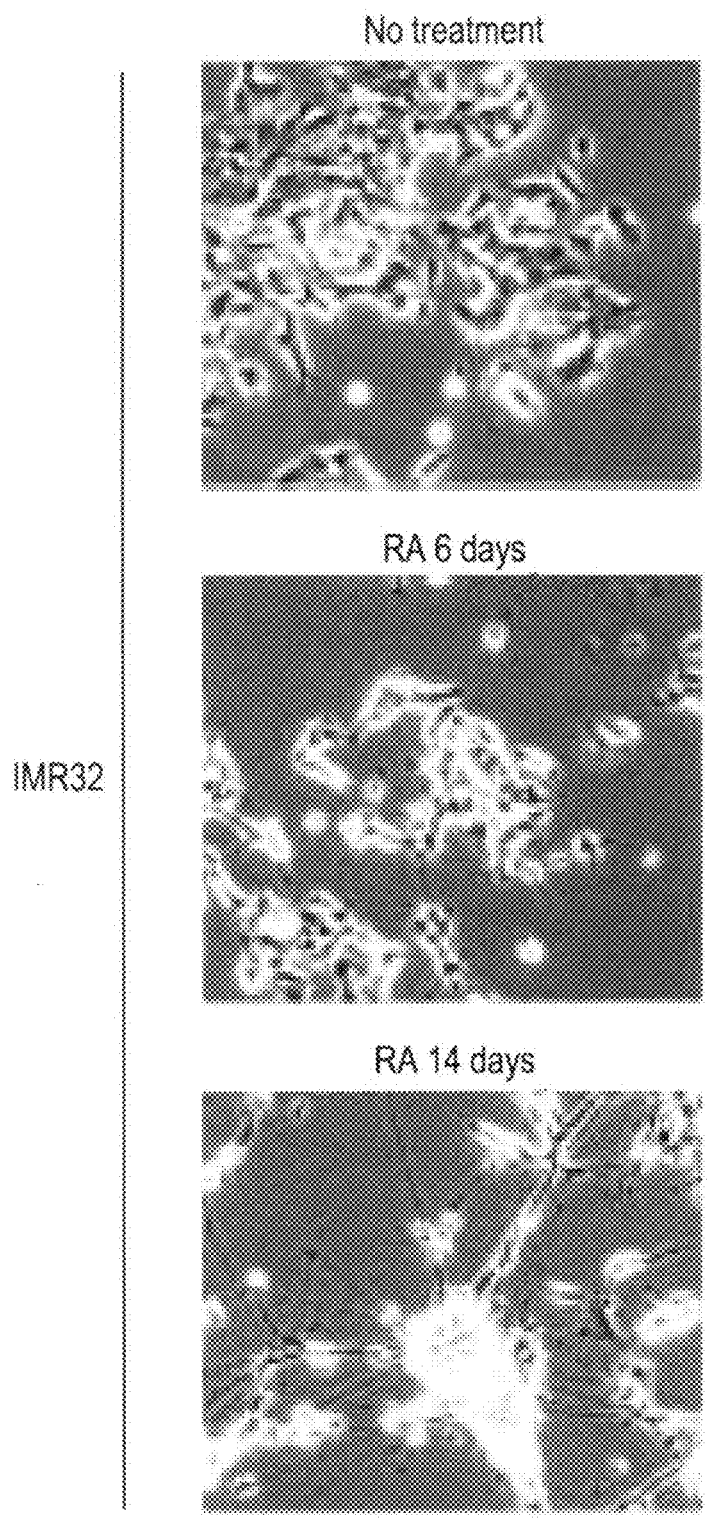

FIG. 13(a) shows changes in cellular morphology upon induction of differentiation of IMR32 cells. The cells were treated with 10 uM of retinoic acid (RA) for 14 days. The photograph shows a phase contrast microscopic image.

Figure 13B:

FIG. 13(b) shows MYCN expression 0, 6, and 14 days after treatment with RA analyzed via Western blot analysis.

Figure 13C:
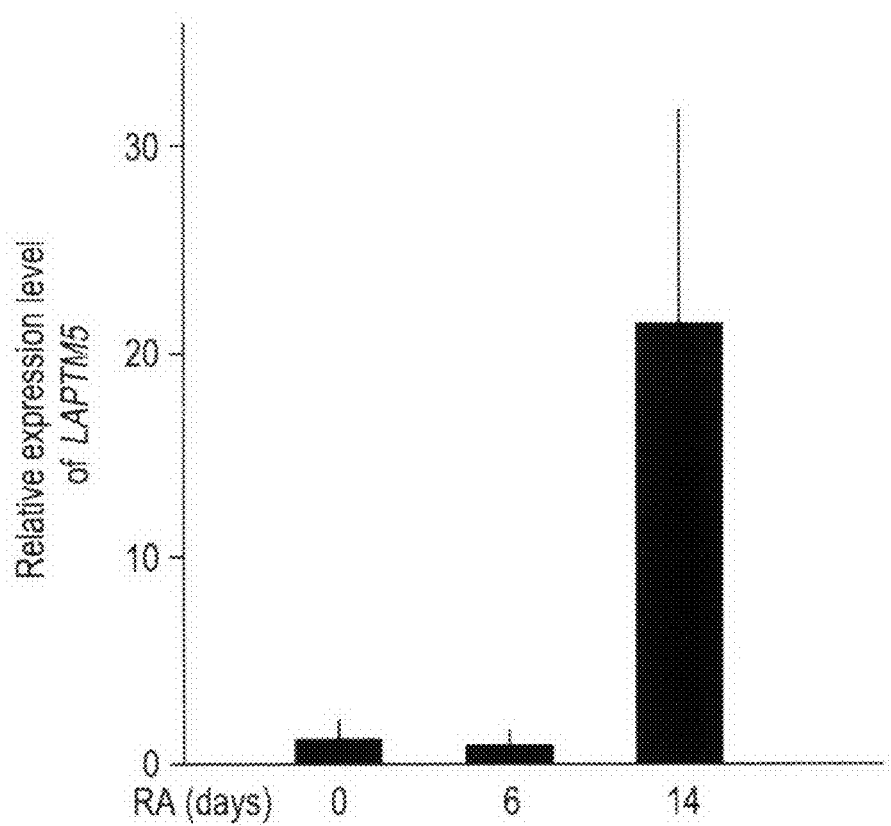

FIG. 13(c) The LAPTM5 expression levels 0, 6, and 14 days after treatment with RA analyzed via quantitative RT-PCR.

Figure 14:
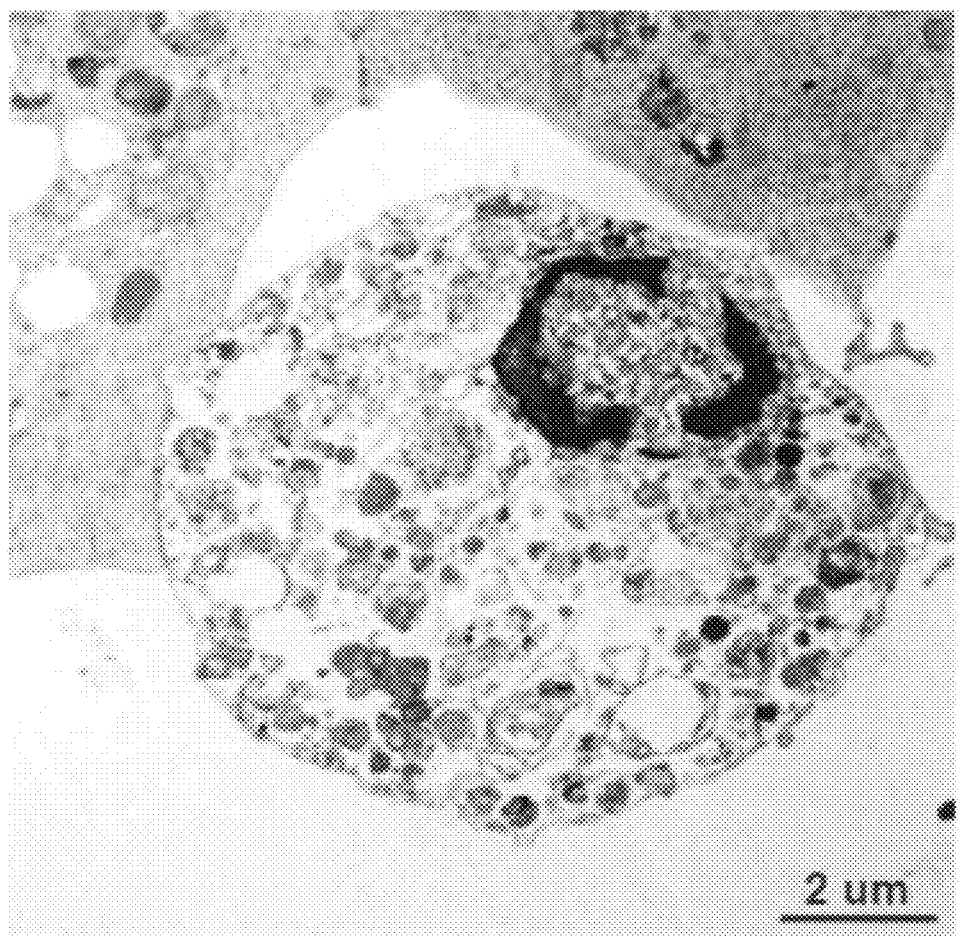

FIG. 14 shows an electron microscopic image showing necrosis in Ad-LAPTM5-infected GOTO cells. Cytoplasmic vacuolation and a tigroid pattern of a nucleus are observed.

FIG. 15 shows LAPTM5-induced cell death in cell lines derived from cancer species other than neuroblastoma cells.

Figure 15A:
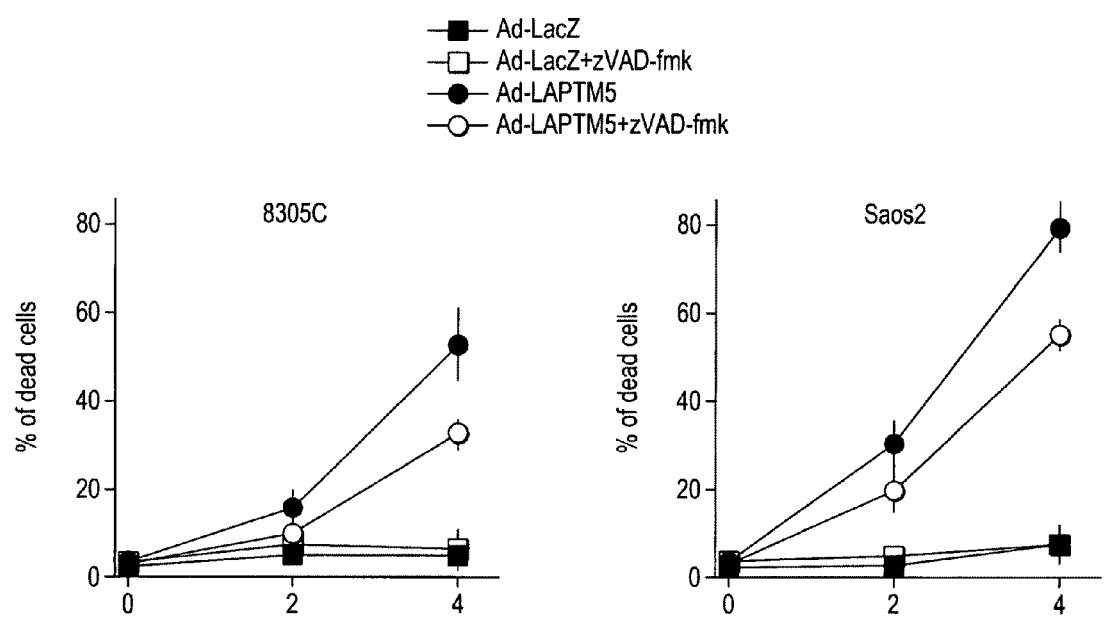

FIG. 15(a) shows 8305C (undifferentiated carcinoma of thyroid: $2\times10^4$ cells/well) and SaoS2 (osteogenic sarcoma: $2\times10^4$ cells/well) sowed on 24-well plates, which had been infected with 10 MOIs of LacZ (Ad-LacZ) or LAPTM5 (Ad-LAPTM5). The dead cells were assayed via trypan blue exclusion 2 days and 4 days after infection. A vertical line represents the standard deviation of two experiments.

Figure 15B:
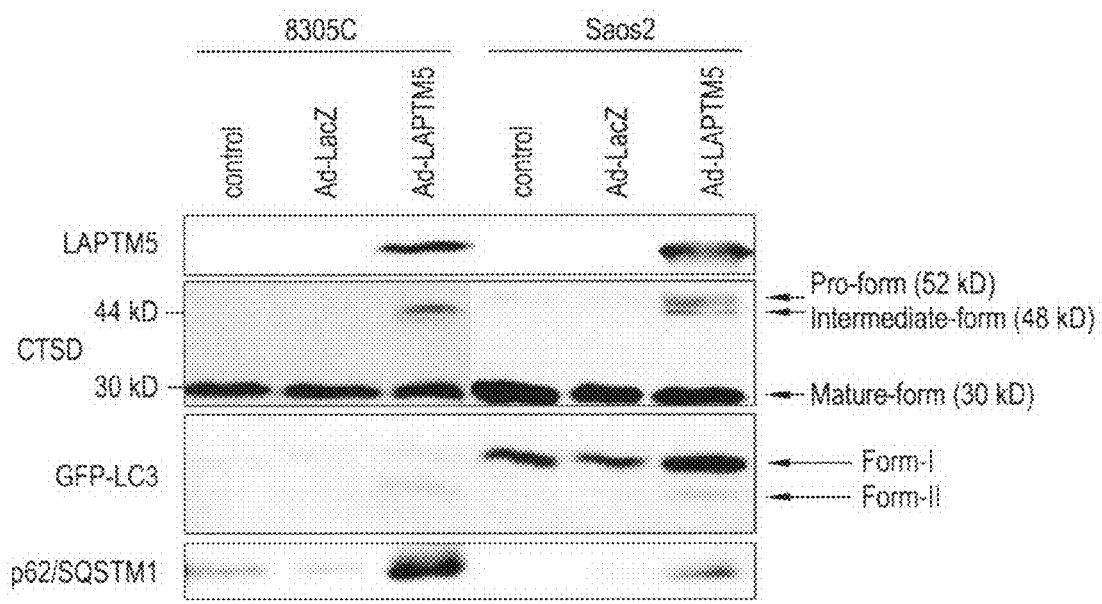

FIG. 15(b) shows detection of GFP-LC3 type II proteins, accumulation of p62/SQSTM1, and an increase in activated forms of CTSD in Ad-LAPTM5-infected 8305C cells or SaOS2 cells. The 8305C cells or SaOS2 cells ($2\times10^4$ cells/well) that stably express GFP-LC3 and that have been sowed on a 24-well plate were infected with 10 MOIs of Ad-LacZ or Ad-LAPTM5, the samples were prepared 4 days later, and Western blot analysis was performed using relevant antibodies.

Figure 16:
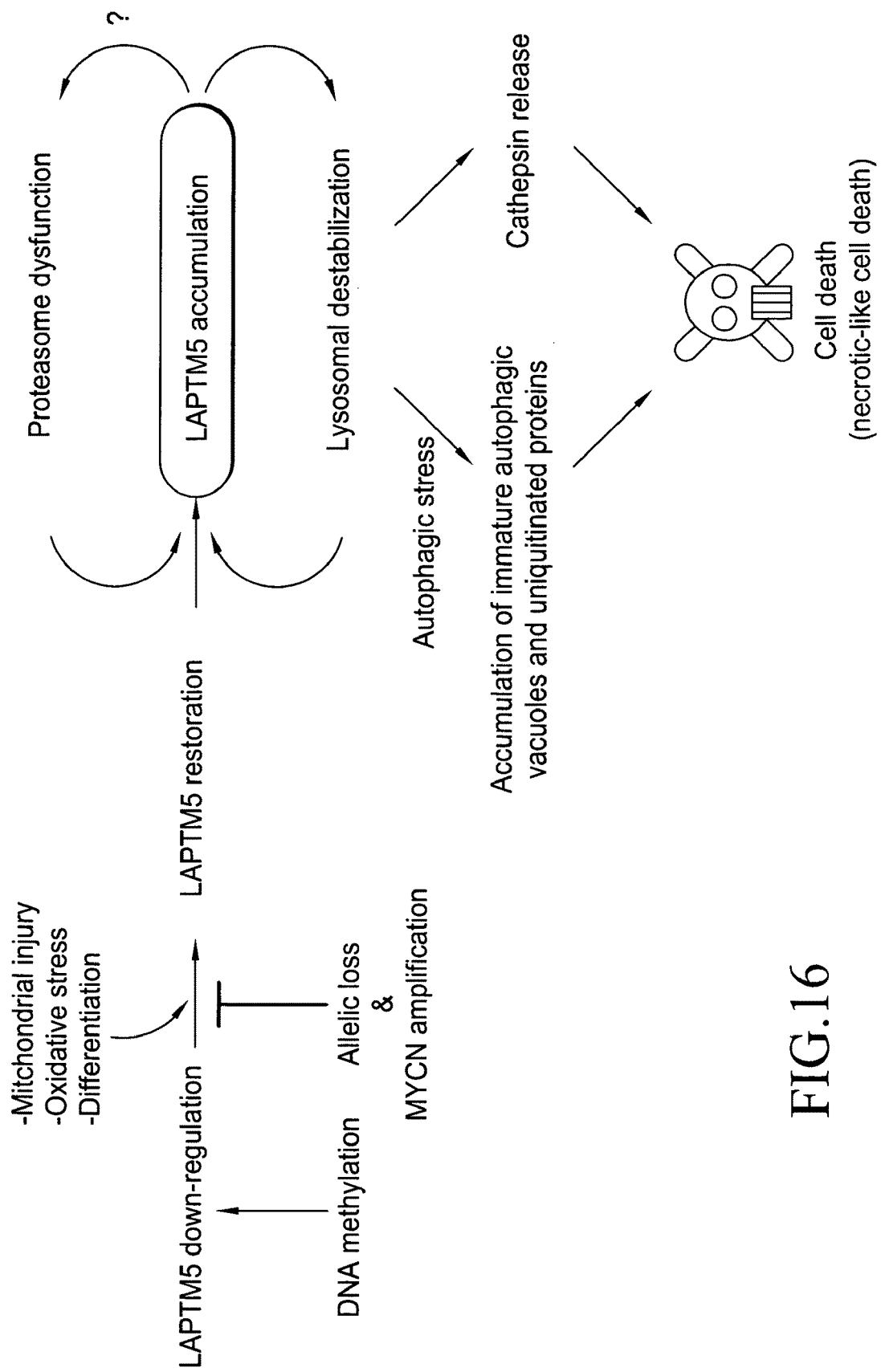

FIG. 16 is a hypothetic diagram showing the molecular mechanism of LAPTM5-induced cell death upon NB tumor regression.

BEST MODES FOR CARRYING OUT THE INVENTION (1) Method for Detecting Cancer

The method for detecting cancer of the present invention is characterized in that activation or inactivation of the lysosomal-associated protein multispanning transmembrane 5 (LAPTM5) gene and amplification of the MYCN gene are detected and thus the malignancy and the process of spontaneous regression in specimens is evaluated.

As described above, the detection method is characterized in that activation or inactivation of the LAPTM5 gene in neuroblastoma is detected via immunohistological staining in neuroblastoma tissue using the LAPTM5-specific antibody or a method for detecting various methylated conditions using the LAPTM5-specific primer.

A target neuroblastoma in which activation or inactivation of the LAPTM5 gene is to be detected is preferably a biopsy tissue cell derived from a specimen donor.

This biopsy tissue cell is identified to be a lesion tissue, when a lesion suspected to be undergoing canceration is observed in the adrenal gland or sympathetic ganglia, or neuroblastoma, as a result of the test or other means. Tissue or the like of neuroblastoma that is required to be subjected to evaluation of the malignancy or advancement can be the primary target.

When inactivation of the LAPTM5 genes is observed in "the lesion tissue, when a lesion suspected to be undergoing canceration is observed in the adrenal gland or sympathetic ganglia, or neuroblastoma, as a result of the test or other means" by the detection method of the present invention, the lesion tissue is found to be advancing toward canceration or to have developed cancer, and the malignancy is found to be increasing. This indicates a necessity of prompt full-scale therapy (e.g., removal of lesions via surgery or full-scale chemotherapy).

When inactivation of the LAPTM5 genes is observed in "neuroblastoma tissue that is identified to be neuroblastoma but required to be subjected to evaluation of the malignancy or advancement," the malignancy of cancer tissue is found to be increasing, which indicates the necessity of prompt and full-scale therapy (e.g., removal of lesion via surgery or full-scale chemotherapy). When a site in which the LAPTM5 gene is activated is found, however, the tumor may undergo spontaneous regression, and selection of therapy other than surgical removal (e.g., follow-up observation) should be taken into consideration. Neuroblastoma tissue that is obtained as a specimen may be subjected to an adequate treatment, such as preparation of DNA or RNA from the obtained tissue, and it may then be used as a target of the detection method of the present invention.

(i) Detection of Deletion of LAPTM5 Gene

Examples of representative techniques that can directly detect deletion of the LAPTM5 gene include comparative genomic hybridization (CGH) and fluorescence in situ hybridization (FISH). The detection method according to this embodiment can detect the presence or absence of the LAPTM5 gene; i.e., deletion of such gene, by performing FISH by labeling bacterial artificial chromosome (BAC) DNA, yeast artificial chromosome (YAC) DNA, and P1-drived artificial chromosome (PAC) DNA (hereafter it may be referred to as BAC DNA or the like) having the LAPTM5 genes.

It is preferable and practical that the method according to the above embodiment be carried out with the use of a genomic DNA-fixed matrix. The amount of BAC DNA or the like that is commonly obtained is too small to produce a large number of genomic DNA-fixed matrices and to put the same to a practical use. Thus, such DNA needs to be obtained as a gene amplification product (this process of gene amplification is also referred to as "infinite amplification"). Upon infinite amplification, BAC DNA or the like is first digested with a four-nucleotide recognition enzyme such as RsaI, DpnI, HaeIII, or the like, followed by ligation with the addition of an adapter. An adapter comprises oligonucleotides having 10 to 30 nucleotides and preferably 15 to 25 nucleotides. Double strands of such adapter have sequences complementary to each other. After annealing, the 3' end of one of the oligonucleotides, at which a blunt end is formed, must be phosphorylated. Next, a primer having a sequence identical to the other oligonucleotide of the adapter is used for amplification via PCR (polymerase chain reaction). Thus, infinite amplification can be carried out. Meanwhile, it is also possible to use, as a detection probe, an aminated oligonucleotide comprising 50 to 70 nucleotides, which is inherent to BAC DNA or the like.

BAC DNAs or the like subjected to infinite amplification is fixed on a matrix and preferably on a solid matrix. Accordingly, a desired DNA-fixed matrix can be produced. A solid matrix is preferably a glass plate. Further preferably, a solid matrix made of glass or the like is coated via adhesion with poly-L-lysine, aminosilane, gold, aluminum, or the like.

The concentration of DNA subjected to infinite amplification to be spotted on a matrix is preferably 10 µg/µl to 5 µg/µl, and more preferably 1 ng/µl to 200 ng/µl. The amount of the same to be spotted on the matrix is preferably 1 nl to 1 µl, and more preferably 10 nl to 100 nl. In addition, the size and the shape of each spot that is fixed on the matrix are not particularly limited. In terms of size, such spot may have a diameter of 0.01 to 1 mm, for example. In addition, the shape of such spot may be a circle or elipse from an overhead view. The thickness of a dry spot is not particularly limited; however, it may be 1 to 100 µm. Further, the number of spots is not particularly limited; however, it may be 10 to 50,000 spots, and more preferably 100 to 5,000 spots on the matrix used. DNAs are spotted singly to quadruplicate. However, preferably, DNAs are spotted in duplicate or triplicate.

Regarding preparation of dry spots, it is possible to produce dry spots by, for example, spotting BAC DNAs or the like subjected to infinite amplification on a matrix with the use of a spotter, forming a plurality of spots thereon, and drying the spots. Examples of a spotter that can be used include an inkjet printer, a pin-array printer, and a bubble jet (trademark) printer. Among them, an inkjet printer is preferably used. For instance, GENESHOT (NGK INSULATORS; Nagoya, Japan) or the like can be used.

As described above, it is possible to produce a desired DNA-fixed matrix by fixing BAC DNAs or the like subjected to infinite amplification onto a matrix, and preferably, onto a solid matrix.

In addition, an example of a means of directly detecting the LAPTM5 gene deletion is the Southern blot method. In the Southern blot method, the existence of the gene in a specimen is detected by separating and fixing genomic DNA obtained from the specimen and detecting hybridization of such genomic DNA with the LAPTM5 gene.

(ii) Detection of LAPTM5 Gene Inactivation

It has been reported that transcriptional inactivation occurs when a CpG-rich promoter and an exon region are densely methylated (Bird A R, et al., Cell, 99, 451-454, 1999). In the cases of cancer cells, CpG islands are frequently and densely methylated compared with other regions, and thus hypermethylation of a promoter region is deeply involved in the inactivation of a cancer-suppressing gene in cancer (Ehrlich M., et al, Oncogene, 21, 6694-6702, 2002).

A demethylating reagent (e.g., 5-azadeoxycytidine) may be allowed to act on the specimen cells (i.e., primary cancer cells derived from cancer tissue), which had been found to experience a decreased LAPTM5 gene expression level, in an attempt of recovering the gene expression level. When the LAPTM5 gene expression level is recovered by allowing a demethylating reagent to act on the specimen cells, accordingly, methylation of CpG islands is a cause of inhibition of the gene expression in the specimen cells. Thus, administration of a drug having demethylation effects to a specimen donor can yield beneficial antitumor effects.

(iii) Detection of LAPTM5 Gene Activation

Figure 2A:
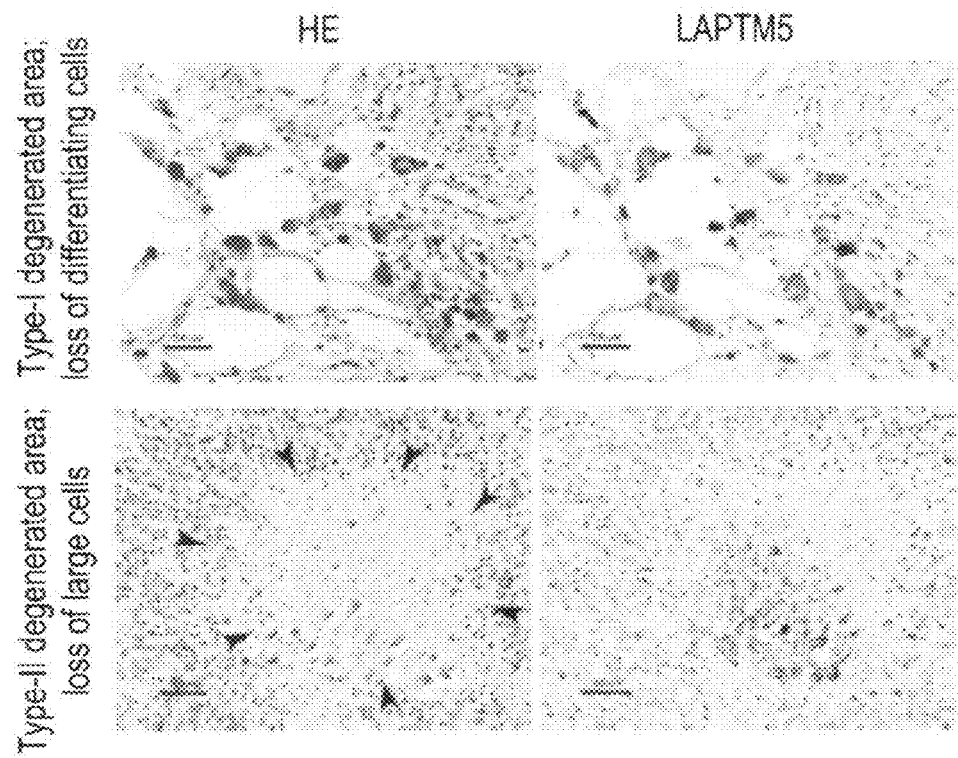
FIG. 2(a) shows the immunohistologically stained image of LAPTM5 at the degenerating site in the tumor specimen section in stage 1. Continued sections were stained with hematoxylin-eosin (left) or with the LAPTM5 antibody (right). The upper portion shows the stained image of the degenerating site where cells showing differentiation tendency are collectively dropped (the type I degenerating site). The lower portion shows the stained image of the degenerating site where undifferentiated cells are collectively dropped (the type II degenerating site). The region surrounded by arrows shows a typical type II degenerating site.
Figure 2B:
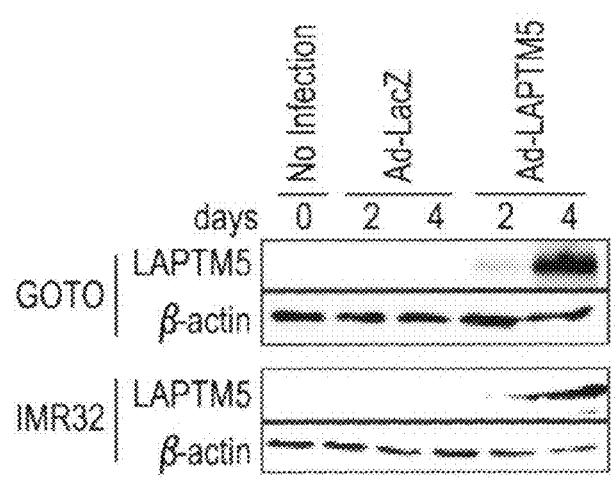
FIG. 2(b) shows Western blot analysis of the GOTO cells and IMR32 cells infected with adenoviruses. The GOTO cells ($5 \times 10^4$ cells/well) sowed on a 24-well plate were infected with 10 MOIs of LacZ(Ad-LacZ) or LAPTM5 (Ad-LAPTM5) adenoviruses and the IMR32 cells ($2 \times 10^4$ cells/well) sowed on a 24-well plate were infected with 4 MOIs of LacZ(Ad-LacZ) or LAPTM5 (Ad-LAPTM5) adenoviruses. The entire cell extracts (30 µg each) 2 days and 4 days after infection were subjected to 12% SDS-PAGE electrophoresis and assayed via immunoblotting using antibodies against LAPTM5 or β-actin (the internal standard of the amount of proteins). The representative results of two independent experiments are shown.

When a tumor degenerating site in which a tumor cell found to be positive for the LAPTM5 gene as shown in FIG. 2a is present and the cell is dropped therefrom is detected via immunohistological staining of a tumor tissue section using a specific antibody, such tumor is considered to be in the process of spontaneous regression.

(2) A Method for Suppressing Cell Growth and a Suppressor for Cell Growth

The present invention further provides a method for suppressing cell growth which comprises introducing in vivo or in vitro the LAPTM5 gene or a protein which is the LAPTM5 gene expression product, into the cell, and a suppressor for cell growth which comprises such gene or protein.

When handling the LAPTM5 gene, cDNA obtained from cultured cells via a technique known in the art or cDNA enzymatically synthesized via PCR or other means may be used. When obtaining DNA via PCR, PCR is carried out with the use of human chromosome DNA or cDNA library as a template and primers designed so as to amplify the target nucleotide sequences. The DNA fragment amplified via PCR can be cloned into an adequate vector that can amplify the gene of interest in a host cell such as $E.$ $coli.$ Procedures, such as preparation of probes or primers for LAPTM5 gene detection and cloning of target genes, are known in the art. For example, such procedures can be carried out in accordance with the method described in Molecular Cloning: A laboratory Manual, $2^{nd}$ Ed., Cold Spring Harbor Laboratory, Cold Spring Harbor, N.Y., 1989, Current Protocols in Molecular Biology, Supplements 1 to 38, John Wiley & Sons, 1987-1997).

The LAPTM5 gene can be incorporated into a vector and used in the form of a recombinant vector. A virus vector or an expression vector for an animal cell may be used, with a virus vector being preferable. Examples of virus vectors include retrovirus, adenovirus, adeno-associated virus, baculovirus, vaccinia virus, and lentivirus vectors. Use of the retrovirus vector is particularly preferable because the virus genome thereof is incorporated into a host chromosome, following cell infection, and it is capable of stable and long-term expression of a foreign gene that has been incorporated into the vector.

Examples of expression vectors for animal cells that can be used include pCXN2 (Gene 108, 193-200, 1991), PAGE207 (JP Patent Publication (kokai) No. H6-46841 A (1994)), and a modified form thereof.

The recombinant vector can be produced by introducing the gene into an adequate vector for transformation and culturing the resulting transformant. When a recombinant vector is a virus vector, such vector is introduced into an animal host cell capable of virus production. Examples include COS-7 cells, CHO cells, BALB/3T3 cells, and HeLa cells. Examples of hosts for retrovirus vectors include ΨCRE, ΨCRIP, and MLV. An example of hosts for adenovirus and adeno-associated virus vectors is the 293 cell derived from the human embryonic kidney. The virus vector can be introduced into an animal cell by the calcium phosphate method, for example. When a recombinant vector is an expression vector for an animal cell, such vector can be introduced into a host cell, such as $E.$ $coli$ K12, HB101, and DH5α lines. A technique of $E.$ $coli$ transformation is known to a person skilled in the art.

The obtained transformants are cultured in media under culture conditions suitable for the same. For example, $E.$ $coli$ transformants are cultured in a liquid medium (pH: about 5 to 8) comprising carbon sources, nitrogen sources, inorganic matter, and other substances necessary for growth. Culture is generally conducted at 15° C. to 43° C. for about 8 to 24 hours. In such a case, the target recombinant vector can be obtained via a general DNA isolation/purification technique, following the completion of culture.

Animal cell transformants can be cultured in media, such as 199 medium, MEM medium, or DMEM medium containing about 5% to 20% fetal bovine serum, for example. A pH level of medium is preferably about 6 to 8. Culture is usually conducted at about 30° C. to 40° C. for about 18 to 60 hours. In such a case, virus particles containing the target recombinant vector are released into a culture supernatant. Thus, the recombinant vector of interest can be obtained by concentrating and purifying the virus particles via cesium chloride centrifugation, polyethylene glycol precipitation, filter concentration, or via other means.

The suppressor for cell growth of the present invention can be produced by blending the above gene as an active ingredient with a base that is commonly used for a gene therapy agent. When the above gene is incorporated into a virus vector, virus particles comprising a recombinant vector is prepared and the resultant is blended with a base that is commonly used for a gene therapy agent.

A base that can be blended with the gene or protein as an active ingredient is a base that is commonly used for an injection preparation. Examples include distilled water, a salt solution, such as sodium chloride or a mixture of sodium chloride with an inorganic salt, a solution of mannitol, lactose, dextran, or glucose, an amino acid solution of glycine or arginine, an organic acid solution, and a mixed solution of a salt solution and a glucose solution. Alternatively, an injection preparation in the form of a solution, suspension, or dispersion can be prepared in accordance with a conventional technique known in the art by adding an adjuvant, such as an osmotic pressure regulator, a pH adjuster, vegetable oil, or surfactant, to such base. Such injection preparation can be prepared in the form of a preparation to be dissolved before use via pulverization, lyophilization, or other procedures.

The suppressor for cell growth of the present invention may be administered via conventional systemic administration, such as intravenous or intraarterial administration, or topical administration, such as topical injection or oral administration. Further, the suppressor for cell growth can be administered via conventional systemic or topical administration in combination with, for example, catheterization, gene introduction, or surgical operation.

A dosage of the suppressor for cell growth of the present invention varies depending on the age, sex, and symptoms of a patient, the administration route, the frequency of administration, and a dosage form. Such dosage is generally between about 1 μg/kg and 1,000 mg/kg of the body weight, and preferably between about 10 μg/kg and 100 mg/kg of the body weight, in terms of the weight of the recombinant gene per adult per day. The frequency of administration is not particularly limited.

The present invention is described in greater detail with reference to the following examples, although the present invention is not particularly limited thereto.

EXAMPLES

Example 1

DNA Methylation-Mediated Lowering of LAPTM5 Expression in Neuroblastoma Cell

Figure 6A:
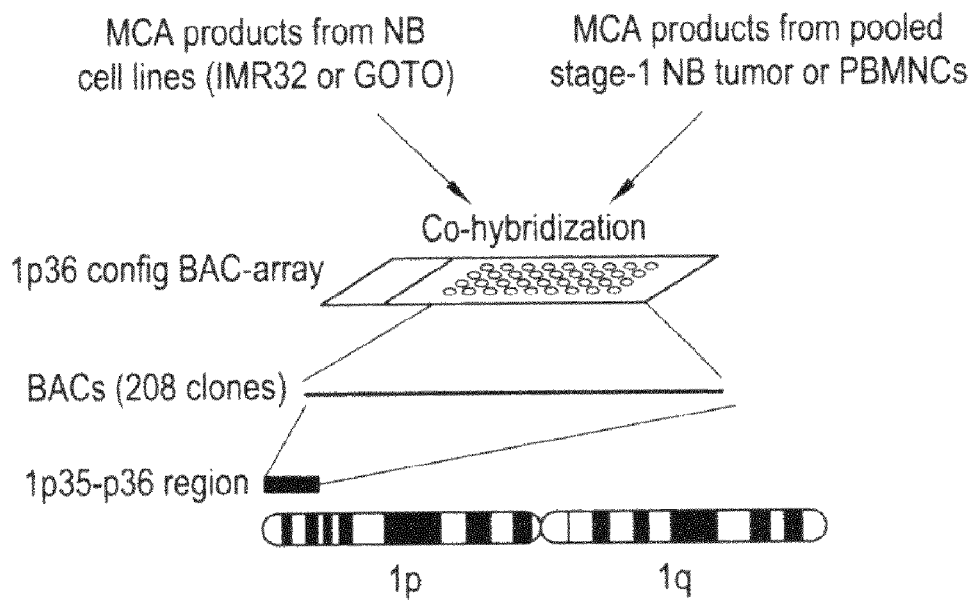
FIG. 6(a) schematically shows BAMCA. DNA fragments were prepared from the neuroblastoma cell line (green) and a reference (red) by the MCA method, labeled with Cy3 or Cy5, and then cohybridized on the 1p36 contig array.

In order to search for neuroblastoma suppressor genes that exhibit a lowered expression level via DNA methylation on the short arm of human chromosome 1 (1p), BAMCA analysis was carried out using the genomic DNA prepared from two types of neuroblastoma cell lines (i.e., IMR32 cells and GOTO cells) and using the 1p36 contig BAC-array (Toyota M. et al., Cancer Res, 2005, 10, 2307-2312, Inazawa J., et al., Cancer Sci, 2004, 95, 559-563, Misawa A. et al., Cancer Res, 2005, 65, 10233-10242, Sugino Y. et al., Oncogene, 2007, 26, 7401-7413, Tanaka K. et al, Oncogene, 26, 6456-6468). As the control, MCA (methylated CpG island amplification) products (Toyota M. et al., Cancer Res, 2005) prepared from neuroblastoma specimens in stage 1 or the normal peripheral blood mononuclear cells (PBMNCs) were labeled with Cy5. As the test samples, MCA products prepared from IMR32 cells and from GOTO cells were labeled with Cy3. Following hybridization by the BAMCA method, the array was scanned with the use of the GenePix 4000B scanner (Axon Instruments, CA, U.S.A.) to monitor the fluorescence derived from Cy3 and Cy5 (FIG. 6a). The obtained results were analyzed using the GenePix Pro4.1 Imaging software (Axon Instruments, CA, U.S.A.). The average of the fluorescent intensity derived from Cy3 was adjusted to the same level with the average of the fluorescent intensity derived from Cy5 to determine the Cy3/Cy5 ratio. When there is no difference in methylation, the ratio is 1. When the ratio was greater than 1.0, it was determined that changes were observed in methylation.

As a result, 3 BAC clones (127J4, 316C6, and 418B22) having the features of the methylated DNA sequences were isolated as the candidates from IMR32 cells and GOTO cells (Table 1).

Figure 6B:
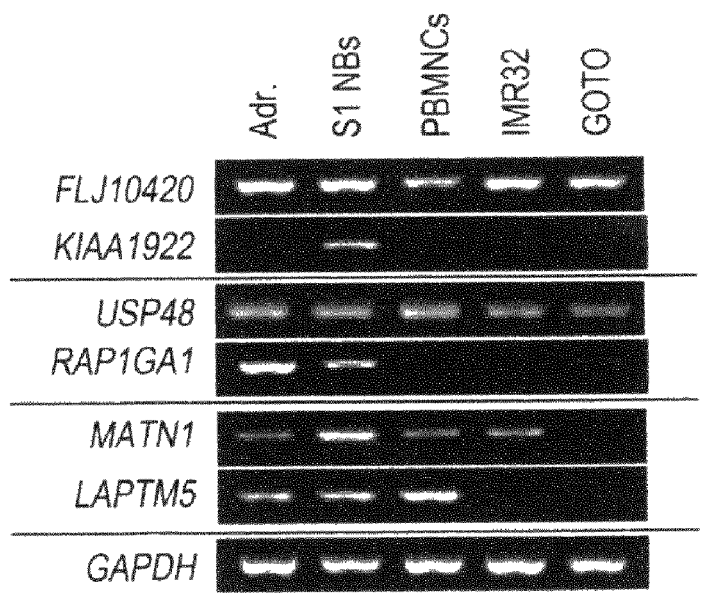
FIG. 6(b) shows screening of the candidate gene via RT-PCR analysis. The GAPDH gene was used as the internal standard. "Adr" represents the normal adrenal gland, and "S1 NBs" represents samples obtained from 5 neuroblastoma tumors in stage 1.

The existence of 6 genes (FLJ10420, KIAA1922, USP48, RAP1GA1, LAPTM5, and MATN1) in these chromosome regions was confirmed using the human genome database (genome.ucsc.edu/). mRNA expressions of these genes were confirmed in IMR32 cells and in GOTO cells via RT-PCR using adequate primers (Table 2) (FIG. 6b, Table 3).

Figure 6C:
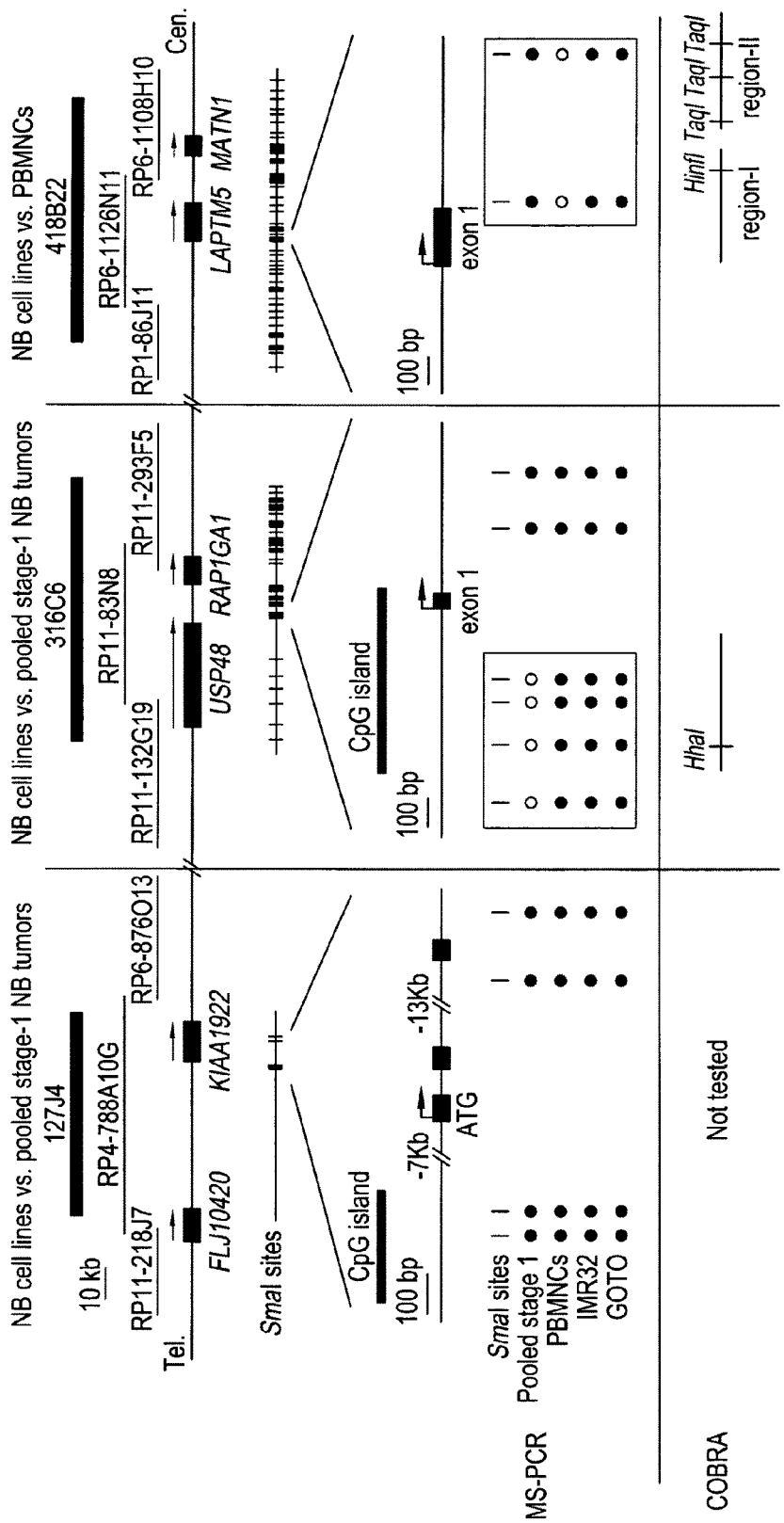
FIG. 6(c) shows the genetic map of three BACs (127J4, 316C6, and 418B22) and the results of methylation-specific (MS)-PCR analysis of the SmaI site in the vicinity of the transcription initiation site of the genes. A black box or bar represents a gene or CpG island. An arrow regarding the initiation site represents a transcription direction. Black and white circles of MS-PCR represent the presence of the PCR product (methylated) and the absence thereof (nonmethylated). A region shown with a gray box represents methylation frequency in the GOTO cells and in the IMR cells in comparison with the references (PBMNCs regarding LAPTM5, and neuroblastoma tumors in stage 1 regarding RAP1GA1).

As a result, expression levels of the 3 genes (KIAA1922, RAP1GA1, and LAPTM5) were found to be lowered in both IMR32 cells and GOTO cells, compared with the neuroblastoma specimen in stage 1 (S1 NBs), normal adrenal gland (Adr), or PBMNCs (FIG. 6b, Table 1). In order to inspect the methylation condition in greater detail, methylation specific (MS)-PCR was carried out to inspect the methylation conditions at the CG site in the SmaI recognition sequence located in the vicinity of the transcription initiation sites of RAP1GA1 and LAPTM5 in IMR32 cells and GOTO cells (FIG. 6c, Table 1). Genomic DNAs (1 μg) of the cells were digested with the methylation-sensitive restriction enzyme SmaI (New England BioLabs) in 40 μl of a reaction solution at 25° C. for 24 hours, and the amplification reaction was performed using adequate primers (Table 2). The methylation conditions of the SmaI sites were determined based on the existence of the PCR product. As a result, methylation of KIAA1922 could not be observed; however, RAP1GA1 and LAPTM5 were found to undergo methylation in IMR32 cells and in GOTO cells.

Figure 6D:
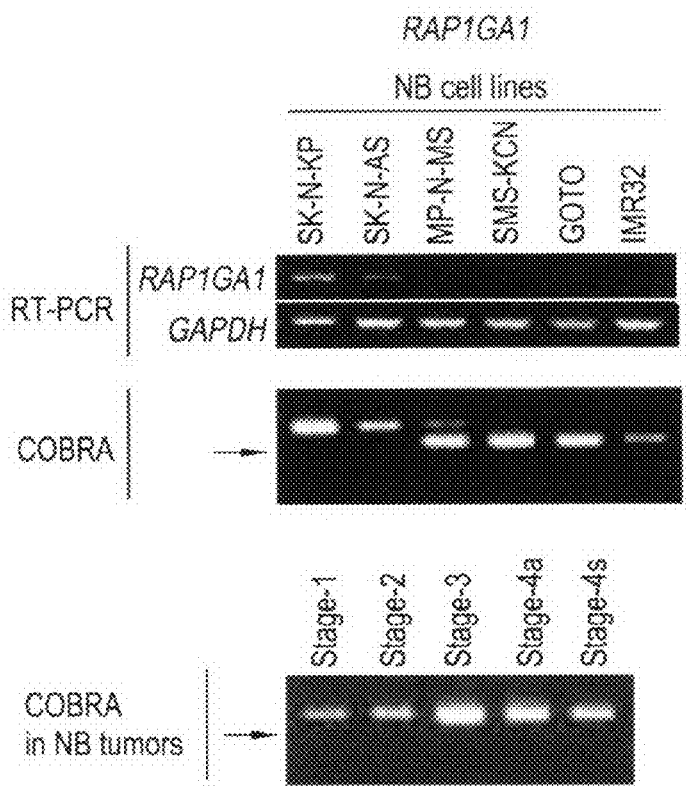
FIG. 6(d) shows representative images obtained via COBRA and RT-PCR analysis of the neuroblastoma cell line and primary tumor for RAP1GA1. The bisulfite-PCR product in the RAP1GA1 region of (c) was digested with HhaI. An arrow represents a band that can be observed when methylated.
Figure 6E:
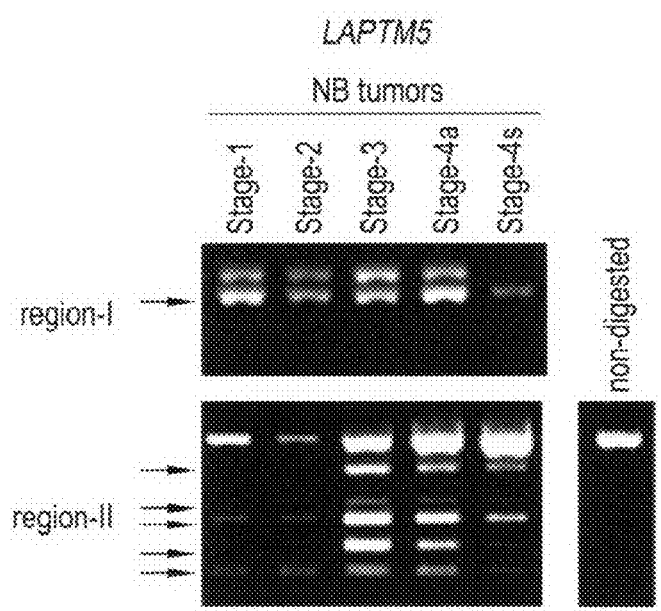
FIG. 6(e) shows a representative image obtained via COBRA of neuroblastoma specimens for LAPTM5. The bisulfite-PCR product in two regions of LAPTM5 of (c) was digested with HinfI (region 1) and with TaqI (region 2). An arrow represents a band that can be observed when methylated.
Figure 6F:
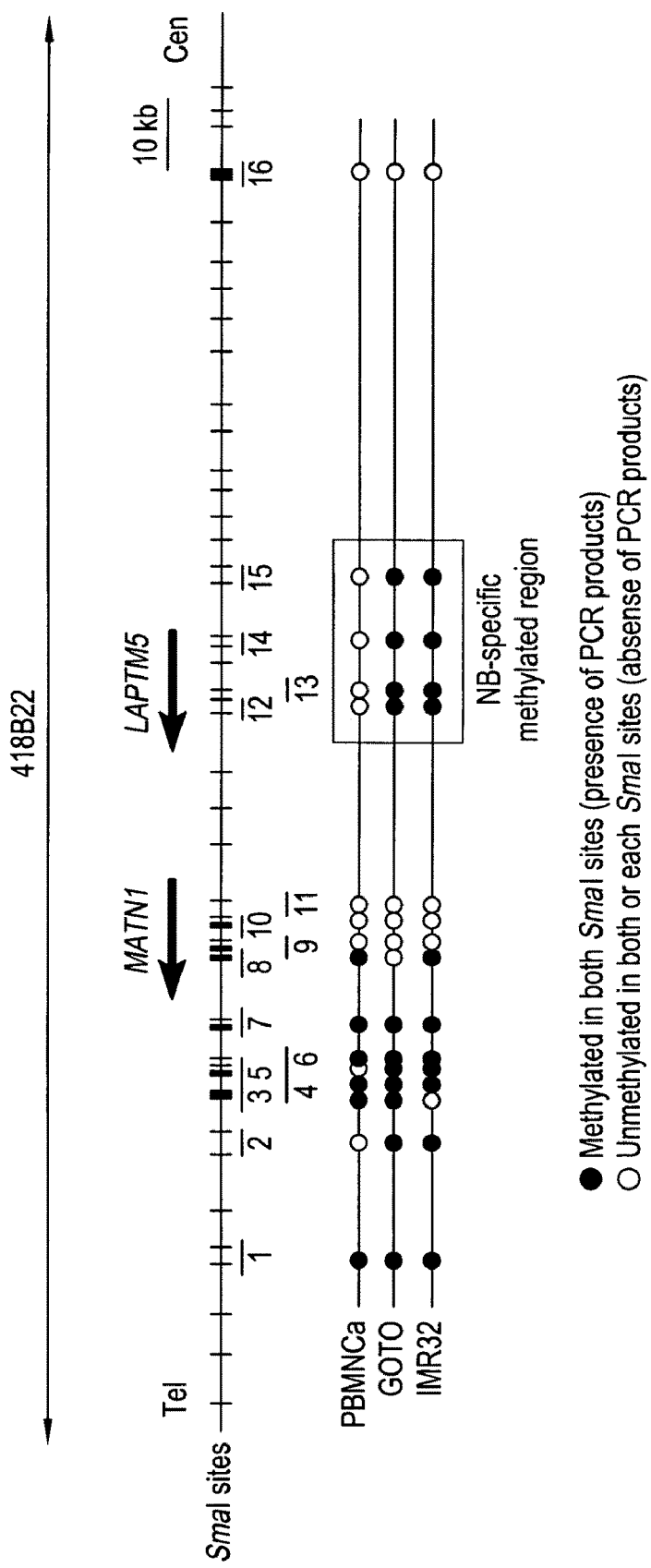
FIG. 6(f) shows methylation conditions of the SmaI site in the BAC clone 418B22 comprising LAPTM5 of PBMNCs and two neuroblastoma cell lines containing GOTO cells and IMR32 cells. Sixteen primer sets were synthesized for PCR in the genomic region containing at least 2 SmaI sites within a region comprising 200 to 2,000 base pairs. PCR was carried out using the SmaI-digested genomic fragment as a template. A black and white circle indicates whether or not the PCR product is methylated or nonmethylated. The region shown with a gray box (containing primers 12 to 16) represents a neuroblastoma-specific methylation region of the LAPTM5 locus.
Figure 6G:
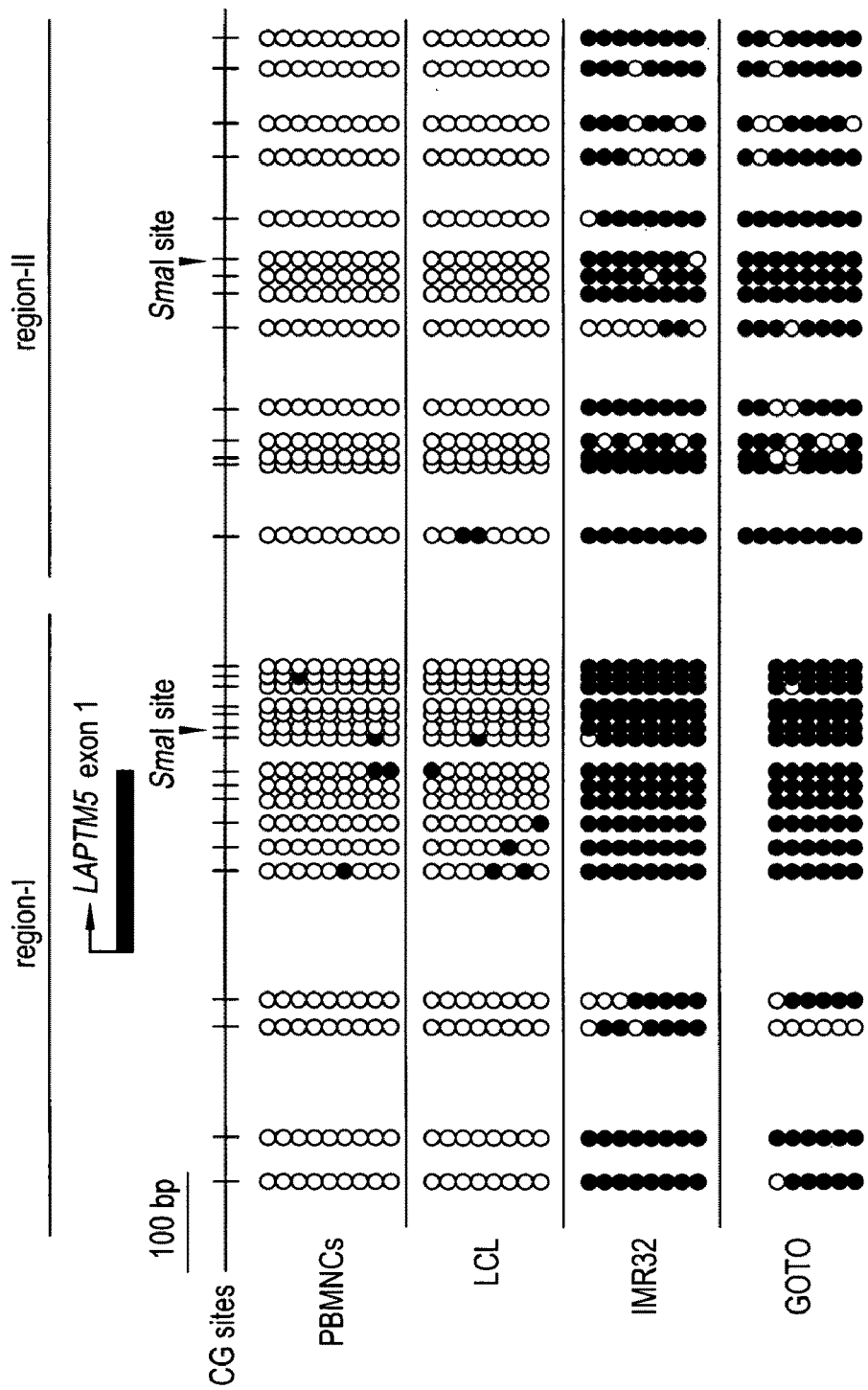
FIG. 6(g) shows methylation conditions at the CG site in the vicinity of the transcription initiation site of the LAPTM5 gene. A total of 32 CO sites located within 1 kb from the initiation point were analyzed with the use of 2 primer sets shown in (c) (region I and region II). An arrow indicates the transcription direction at the initiation site. Arrow heads indicating 2 SmaI sites are as demonstrated in (c). Extensive areas of the GOTO cells and of the IMR32 cells were methylated, and lymphocyte cell lines (LCL) transformed with PBMNCs and EBV were not substantially methylated.

Further, the methylation conditions of the 2 genes (RAP1GA1 and LAPTM5) were inspected using 41 types of neuroblastoma specimens in various stages via combined bisulfite restriction analysis (COBRA). Methylation conditions were inspected via COBRA using the EZ DNA methylation kit (Zymo RESEARCH, CA, U.S.A.). The neuroblastoma specimen-derived genomic DNA (2 μg) was treated in sodium bisulfite at 50° C. overnight, and PCR was carried out using primers (Table 2) designed so as to amplify the target methylated DNA. The PCR product was digested with the TaqI restriction enzyme (New England BioLabs) or the HhaI restriction enzyme (New England BioLabs). With the utilization of properties such that TaqI and HhaI do not digest a sequence in which unmethylated cytosine is modified with sodium bisulfite but digest a sequence in which methylated cytosine is not modified with sodium bisulfite, the methylation frequency was inspected. As a result, LAPTM5 was found to frequently undergo methylation in neuroblastoma specimens (FIGS. 6d and 6e). Further, methylation conditions at the SmaI site located in BAC418B22 and methylation conditions at the CG site in the vicinity of the transcription initiation point were analyzed via MS-PCR and bisulfite sequencing. As a result, the LAPTM5 gene locus was found to be methylated in GOTO cells and in IMR32 cells at higher frequency in a wider area, compared with the lymphocyte cell line (LCL) transformed with the PBMNCs or EB virus (FIGS. 6f and 6g). Based on the results, the present inventors determined to focus on LAPTM5 as a candidate gene, the expression of which mediated by methylation of 1p35-p36 in neuroblastoma is to be suppressed.

Figure 1A:
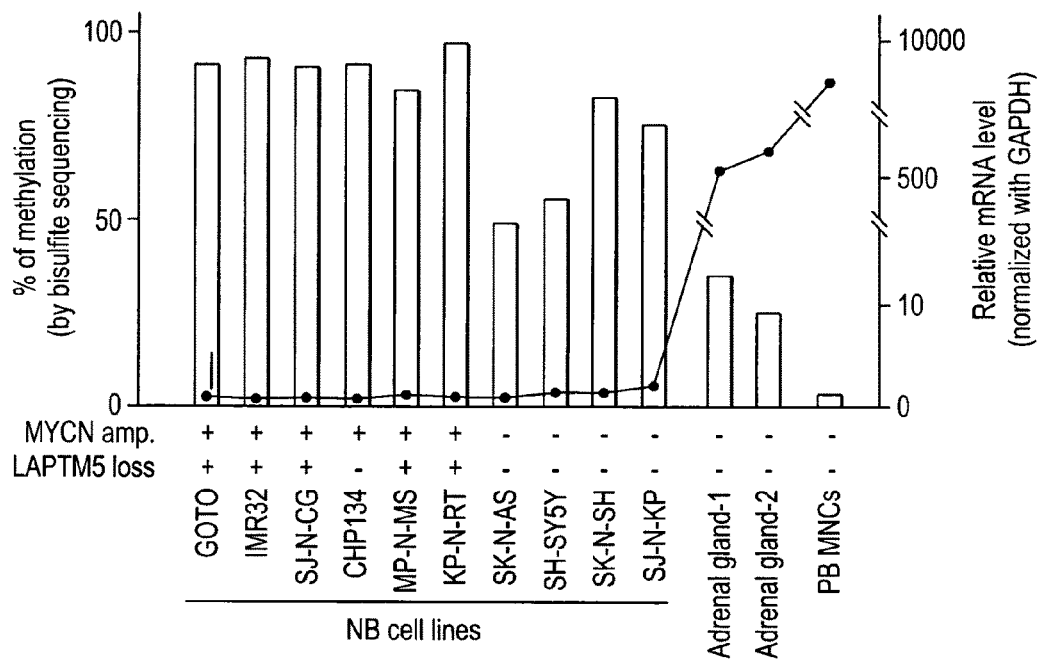
FIG. 1(a) shows methylation frequency and the mRNA level of LAPTM5 in the neuroblastoma cell line. The mRNA level of LAPTM5 in the neuroblastoma cell line with (+) or without (−) amplification of MYCN and with (+) or without (−) deletion of the LAPTM5 gene allele is analyzed via real-time quantitative RT-PCR and is shown with a dot. The mRNA level of LAPTM5 is standardized using the mRNA level of GAPDH. Methylation frequency at 17 CG sites in the vicinity of the transcription initiation point is determined by assaying the transcription initiation site of the LAPTM5 gene via bisulfite sequencing, and the average is shown with a bar chart as the methylation frequency (%).
Figure 6H:
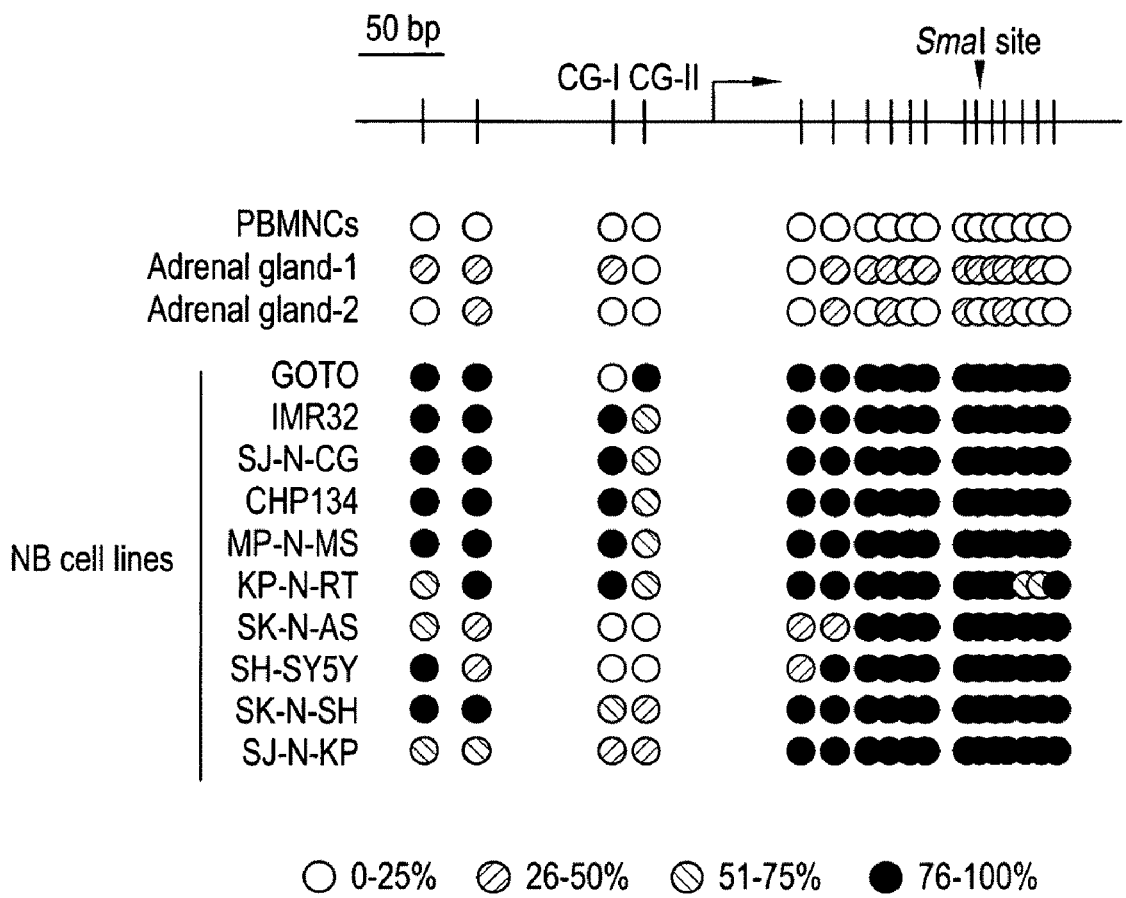
FIG. 6(h) shows the analysis of methylation of the neuroblastoma cell line via bisulfite sequencing. Bisulfite sequencing was carried out at 17 CG sites using the 2 primer sets (region I) as shown in (c). Methylation frequencies are indicated by white (0 to 25%), light gray (26 to 50%), dark gray (51 to 75%), and black (76 to 100%).
Figure 7:
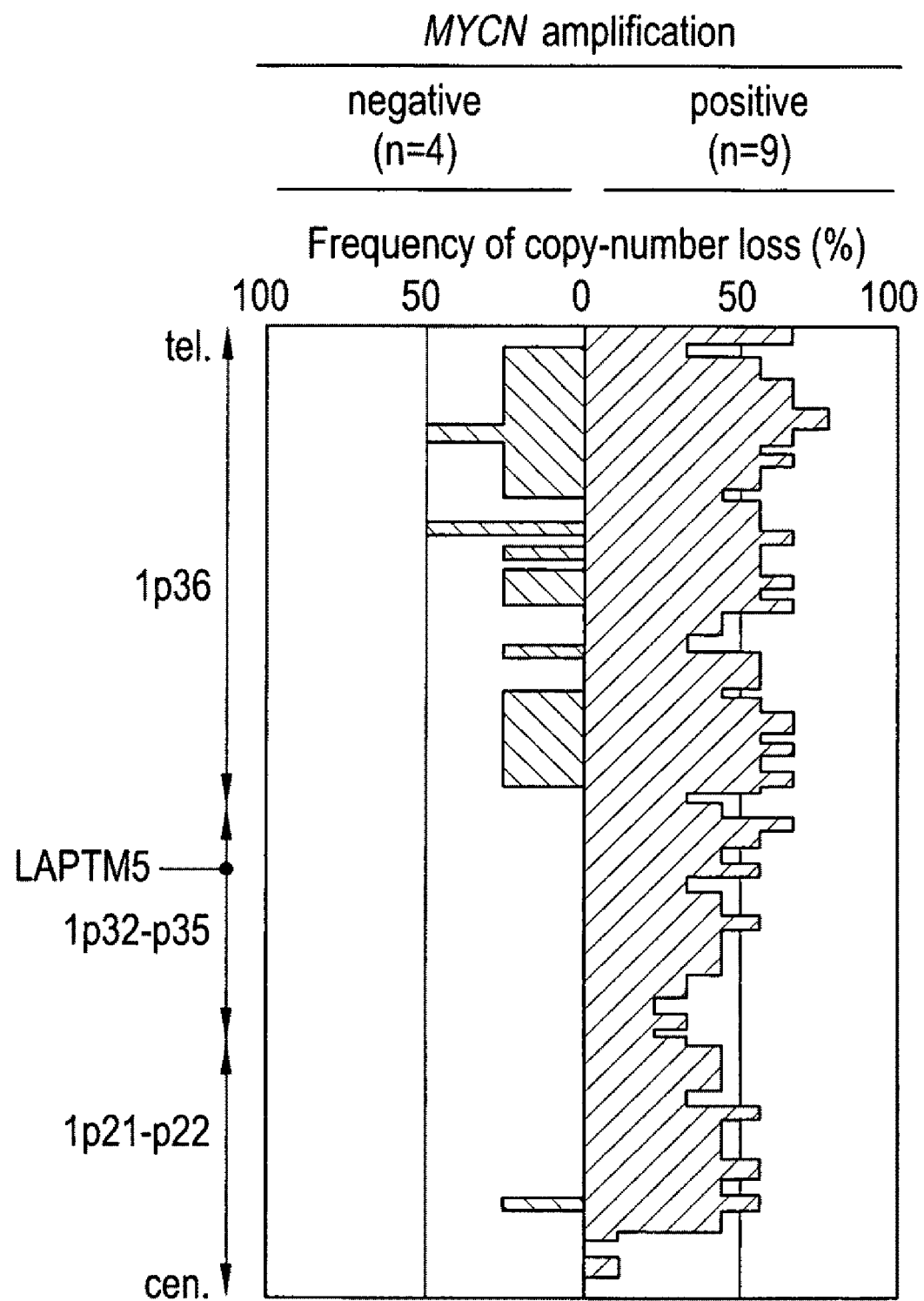
FIG. 7 shows the analysis of changes in DNA copy number in the neuroblastoma cell line.

Quantitative RT-PCR, bisulfite sequencing, the CGH-array method, and FISH analysis were carried out in order to inspect the LAPTM5 gene expression level, methylation frequency, and the copy number in 10 types of neuroblastoma cell lines (SK-N-KP, SK-N-AS, SK-N-SH, SH-SY5Y, KP-N-RT, MP-N-MS, CHP134, SJ-N-CG, IMR32, and GOTO) (FIG. 1a, FIG. 6h, FIG. 7, Table 4). As a result, methylation and lowered LAPTM5 expression levels were detected in all cell lines, regardless of occurrence of MYCN amplification or a reduction in the LAPTM5 copy number.

Figure 1B:
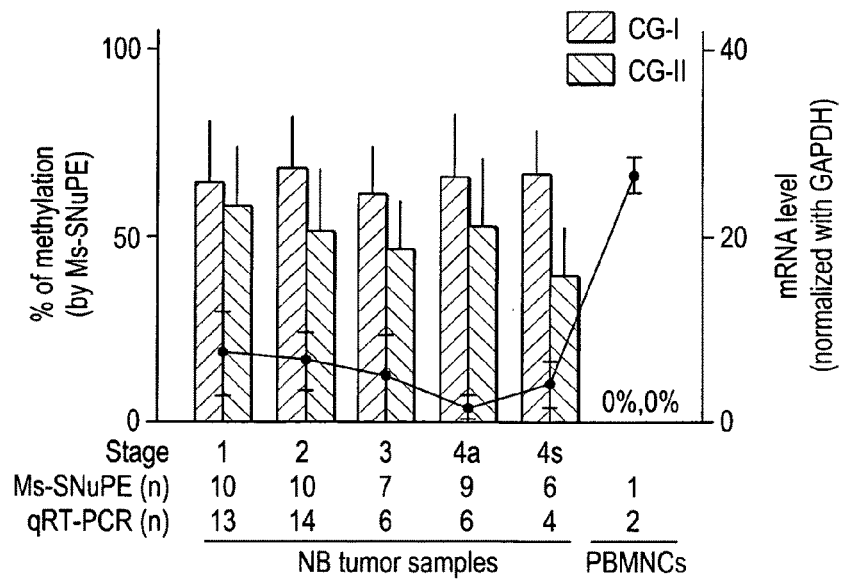
FIG. 1(b) shows methylation frequency and the mRNA level of LAPTM5 in the neuroblastoma specimens in different disease stages. The mRNA level of LAPTM5 is assayed via real-time quantitative RT-PCR and is shown with a dot; and methylation frequency at 2 CG sites (CG-I or CG-II) is assayed via Ms-SNuPE and the result is shown with a dark gray (CG-I) or light gray (CG-II) bar. "n" indicates the number of specimens. A vertical line represents the standard deviation.

Subsequently, quantitative RT-PCR and Ms-SNUPE (i.e., methylation-sensitive single nucleotide primer extension) (Gonzalgo M. L. & Liang G, Nat Protoc, 2007, 2, 1931-1936) were carried out in order to inspect the LAPTM5 expression levels and methylation frequency in neuroblastoma tumor specimens (stages 1, 2, 3, 4S, and 4a) (FIG. 1b, FIG. 8). As a result, the mRNA level was found to be inversely correlated with the methylation conditions in all neuroblastoma tumors, regardless of the prognosis, compared with PBMNCs (FIG. 1b).

The Ms-SNuPE method was carried out by using sodium bisulfite-treated DNA, amplifying the genomic region containing two CG sites via PCR using adequate primers (FIG. 8b, Table 2), and purifying the amplification product via agarose gel electrophoresis. The purified amplification product was subjected to methylation analysis using Ms-SNuPE primers (Table 2) for relevant sites. The Ms-SNuPE product was confirmed via 15% polyacrylamide gel electrophoresis, and the obtained signals were quantified via averaging using the PhosphorImager analysis system (Molecular Dynamics) (FIG. 8b). Methylation was evaluated in accordance with the formula methylated C/(methylated C+nonmethylated T) and determined based on the results of 2 CG sites.

In this case, mRNA was quantified via real-time quantitative PCR (qRT-PCR) with the use of ABI-7900 (Applied Biosystems). As a control, glyceraldehyde-3-phosphate dehydrogenase (GAPDH) was used and the samples were standardized based on the amount of GAPDH. The primer sequences are shown in Table 2.

Figure 1C:
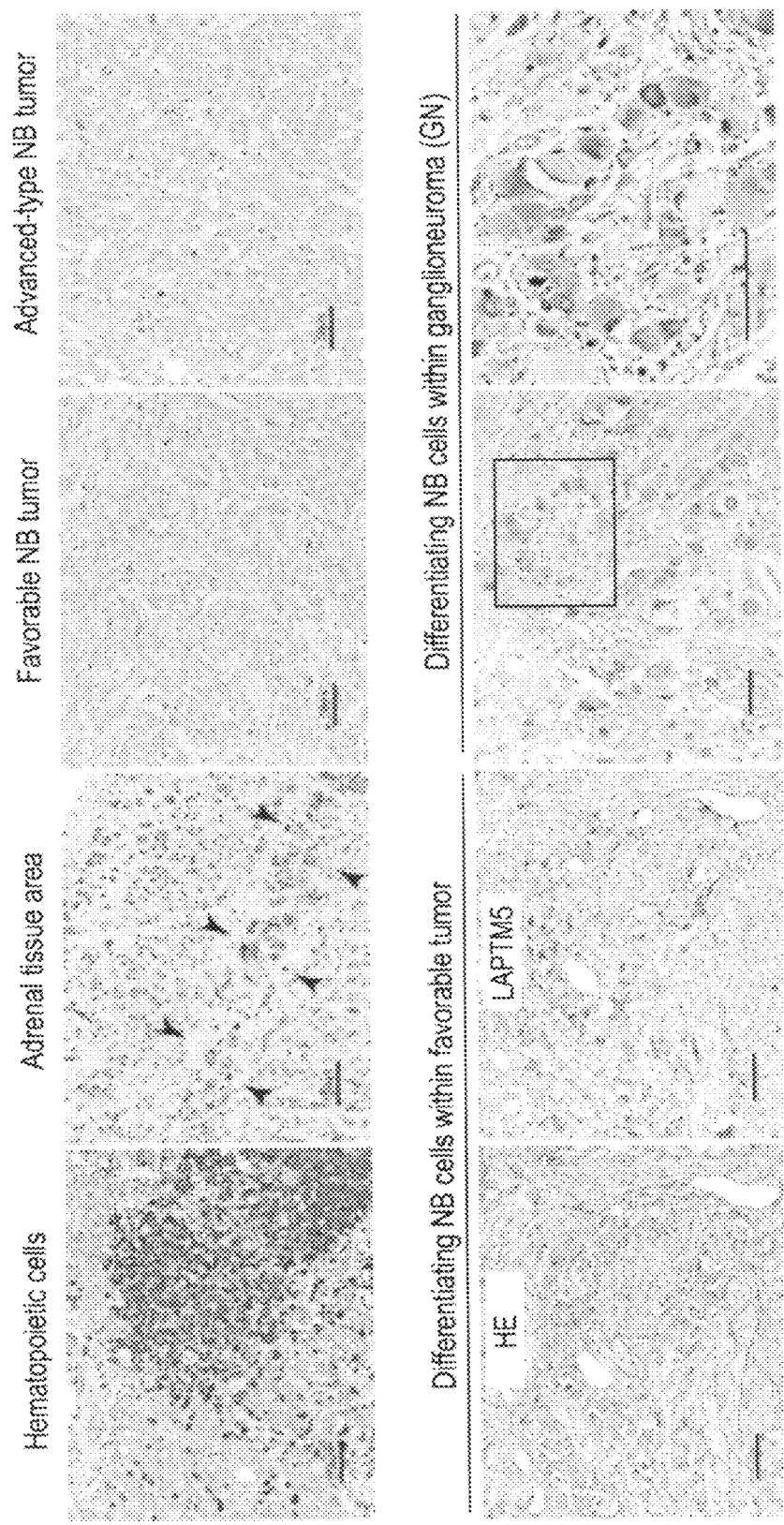
FIG. 1(c) shows the analysis of LAPTM5 expression via immunohistological staining using neuroblastoma tumor specimen sections. The upper portion shows a stained image of LAPTM5 in the blood cell, the adrenomedullary site, the favorable tumor (stage-1), and cancer cell of the MYCN-amplified unfavorable tumor contained in the tumor section. An arrow indicates an adrenomedullary cell. The lower portion shows a stained image of LAPTM5 in differentiated cells contained in favorable tumor specimens or GN specimens and a hematoxylin-eosin stained image thereof. A scale bar represents 50 um.
Figure 1D:
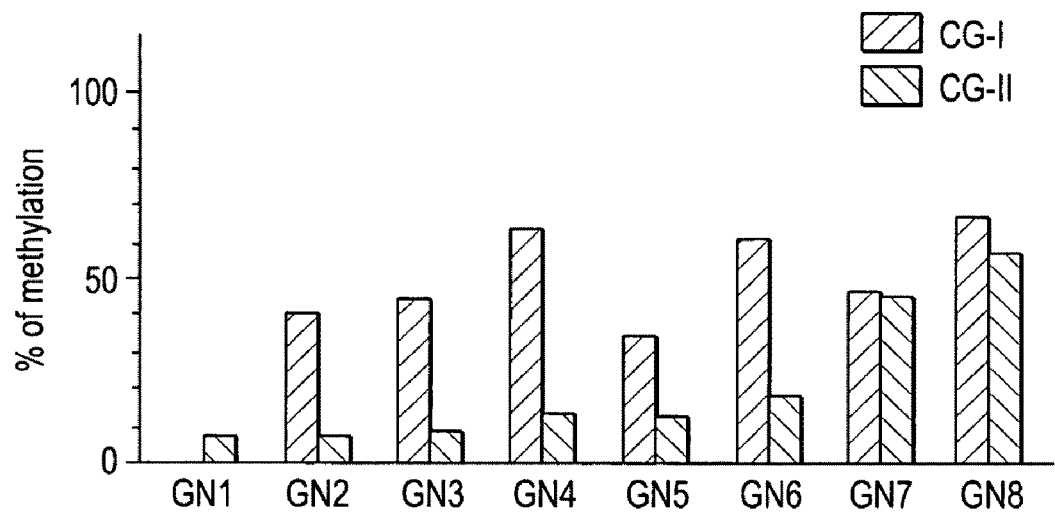
FIG. 1(d) shows methylation frequency in GN. The upper portion shows methylation frequency at 2 CG sites (CG-I or CG-II) assayed via Ms-SNuPE and indicated in a dark gray (CG-I) or light gray (CC-II) bar. The lower portion shows comparison of methylation frequency in neuroblastoma and GN. The average of methylation frequency at CG sites is shown with a bar. "n" indicates the number of specimens. A vertical line represents the standard deviation.
Figure 1D:
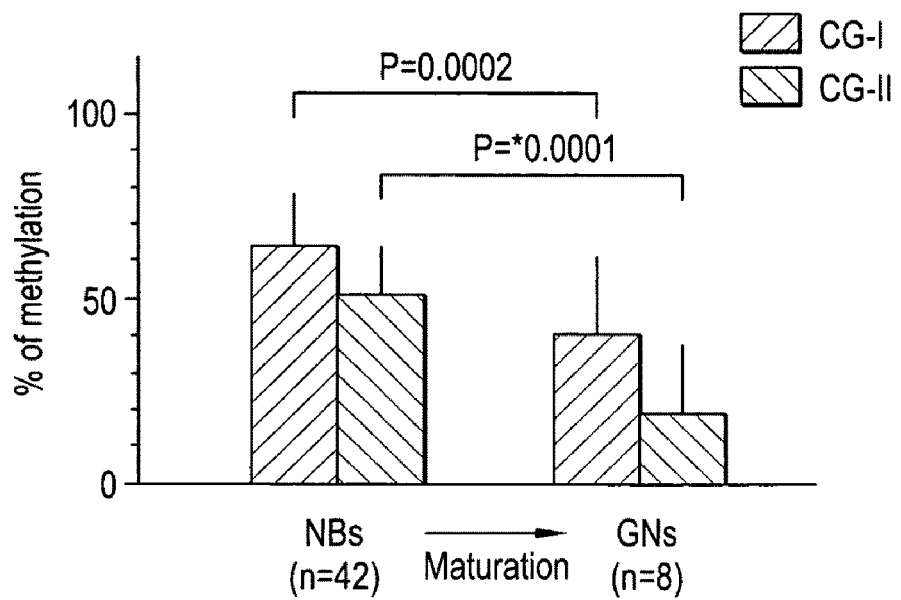
Figure 1C:
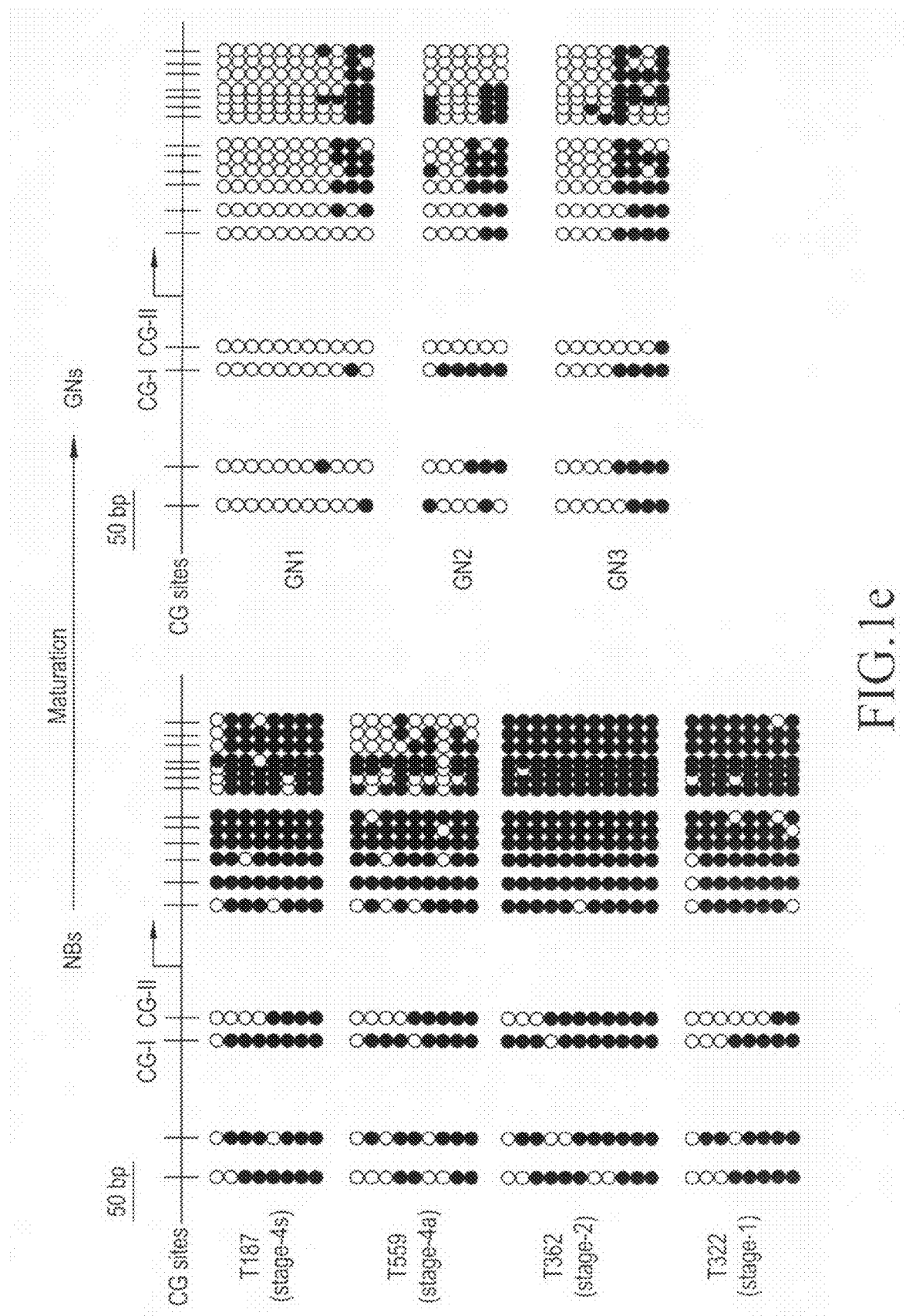

As a result of analysis via immunohistological staining using antibodies specific to LAPTM5 in 71 neuroblastoma specimens, LAPTM5 protein expression levels were found to be lower in all neuroblastoma cancer cells, regardless of the stage, than the expression levels of the positive blood cells and adrenomedullary cells (FIG. 1c). Interestingly, the LAPTM5 expression levels were high in cells that exhibit differentiation tendency contained in favorable specimens or in the differentiated cells contained in completely differentiated and matured GN (FIG. 1c). In differentiated and matured GN, methylation frequency was found to lower than that of neuroblastoma (FIGS. 1d and 1e). This strongly suggests that the LAPTM5 expression levels are lowered by methylation in all neuroblastoma cases.

Example 2

Activation of LAPTM5 in Tumor Degenerating Site and Induction of Caspase-Independent Cell Death Via Forced LAPTM5 Expression As a result of analysis via immunohistological staining using specific antibodies, LAPTM5 expression was found to be activated in degenerating cells in the tumor degenerating sites (type 1: a site from which the group of cells exhibiting differentiation tendency is dropped; type 2: a site from which the group of undifferentiated tumor cells is dropped) (FIG. 2a). The LAPTM5-positive degenerating site was found to more frequently appear in favorable tumors discovered via mass screening (i.e., 42 samples out of 54 samples, 77.8%), compared with unfavorable tumors that have been clinically discovered (i.e., 1 sample out of 17 samples, 5.9%) ($p<0.00001$) (Table 3). Further, a specimen having a LAPTM5-positive tumor degenerating site that is clinically discovered is in the process of pathological differentiation and maturation into GN; i.e., such specimen is considered to be categorized in a group of favorable prognosis. Thus, LAPTM5 was found to be closely correlated with tumor degeneration of spontaneous regression of neuroblastoma. The gene products were deduced to be associated with cell death of neuroblastoma cells. The H-ras that is known to be expressed at high levels in the neuroblastoma degenerating site was found to be coexpressed in the same LAPTM5-positive degenerating site (FIG. 9).

In order to inspect whether or not LAPTM5 expression is associated with cell death of neuroblastoma cells, the influence of forced LAPTM5 expression in the neuroblastoma cell line was inspected using the adenovirus-mediated expression system. Cell death and the survival rate were assayed by sowing the cells on a 24-well plate and infecting the cells with the selected MOIs of viruses (multiplicities of infection; PFU/cell). The number of dead cells was determined via trypan blue exclusion 2 or 4 days after infection. The pan-caspase inhibitor, zVAD-fml, was used at a concentration of 100 μM. At least 200 cells were counted in each experiment. The number of survived cells was determined via colorimetric assay using a water-soluble tetrazolium salt (the cell counting kit-8; Dojindo Laboratories).

Figure 2C:
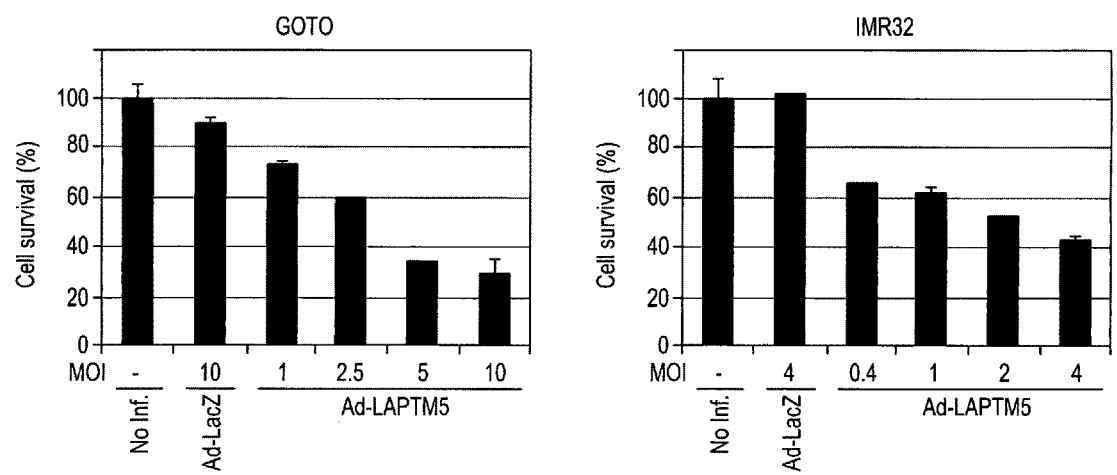
FIG. 2(c) shows the survival rates of adenovirus-infected GOTO cells and IMR32 cells. The cells that had been sowed under the same conditions as in (b) were infected with the same MOIs of Ad-LacZ or Ad-LAPTM5. The rate of surviving cells was determined via colorimetric assay using a water-soluble tetrazolium salt 4 days after infection. A vertical line represents the standard deviation of two experiments. "No inf" represents an uninfected control.
Figure 2D:
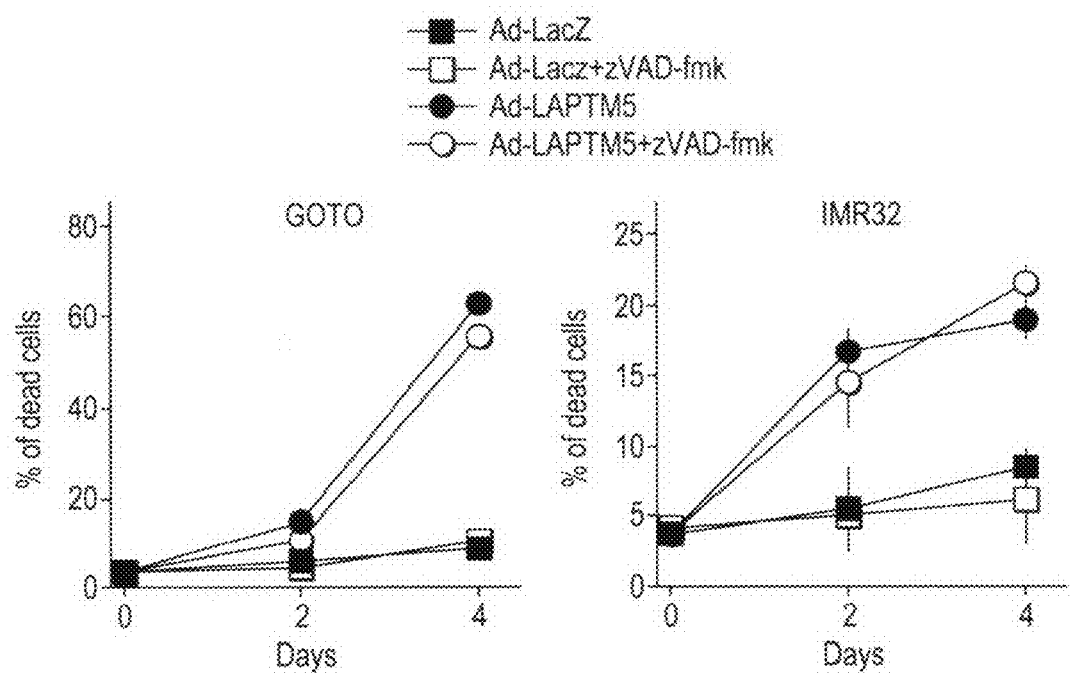
FIG. 2(d) shows frequency of dead cells in adenovirus-infected GOTO cells and IMR32 cells. The cells that had been sowed under the same conditions as in (b) were infected with the same MOIs of Ad-LacZ or Ad-LAPTM5. Also, the cell lines were treated or not treated with the pan-caspase inhibitor, zVAD-fink. The number of dead cells was determined via trypan blue exclusion 2 days and 4 days after infection and was indicated in terms of percentage. A vertical line represents the standard deviation of two experiments.

As a result, strong expression of LAPTM5 proteins was detected in GOTO cells and in IMR32 cells 4 days after infection at a high concentration (FIG. 2b), and the survival rate of the cells was found to decrease in a concentration-dependent-manner in both cell lines that had been infected with adenovirus-LAPTM5 (Ad-LAPTM5) (FIG. 2c). Further, a significant increase of dead cells was observed via Ad-LAPTM5 infection, compared with adenovirus-LacZ (Ad-LacZ) infection, 4 days after infection at a high concentration (FIG. 2d). It was found that death of the cell lines would not be inhibited via treatment using a caspase inhibitor, zVAD-fmk (FIG. 2d). Similar results were obtained when other neuroblastoma cell lines or other cancer-derived cell lines were used (FIG. 15).

These results suggest that LAPTM5 overexpression can induce caspase-independent cell death in neuroblastoma cells.

Figure 2E:
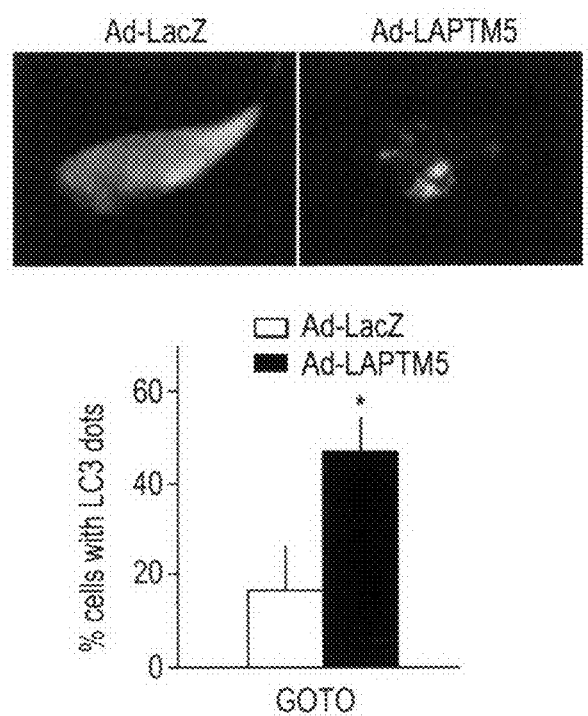
FIG. 2(e) shows intracellular localization of GFP-LC3. The GOTO cells ($5 \times 10^4$ cells/well) sowed on a 24-well plate were infected with 10 MOIs of LacZ (Ad-LacZ) or LAPTM5 (Ad-LAPTM5) adenoviruses. The cells were fixed 4 days thereafter, and a typical image was obtained using a fluorescent microscope. The lower portion represents the frequency of cells in which dot-like localization of GFP-LC3 is observed (%).
Figure 2F:
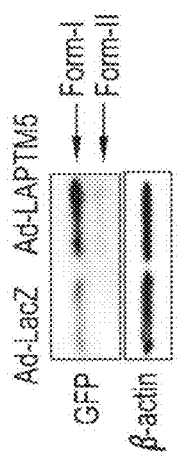
FIG. 2(f) shows detection of GFP-LC3II via Western blotting. The GOTO cells that stably express GFP-LC3 were infected with 10 MOIs of Ad-LacZ or Ad-LAPTM5. The entire cell extract (30 µg each) 4 days after infection was subjected to 12% SDS-PAGE electrophoresis and assayed by GFP or immunoblotting using antibodies against β-actin (the internal standard of the amount of proteins) on a separated membrane. An arrow indicates type I or II of GFP-LC3.
Figure 2G:
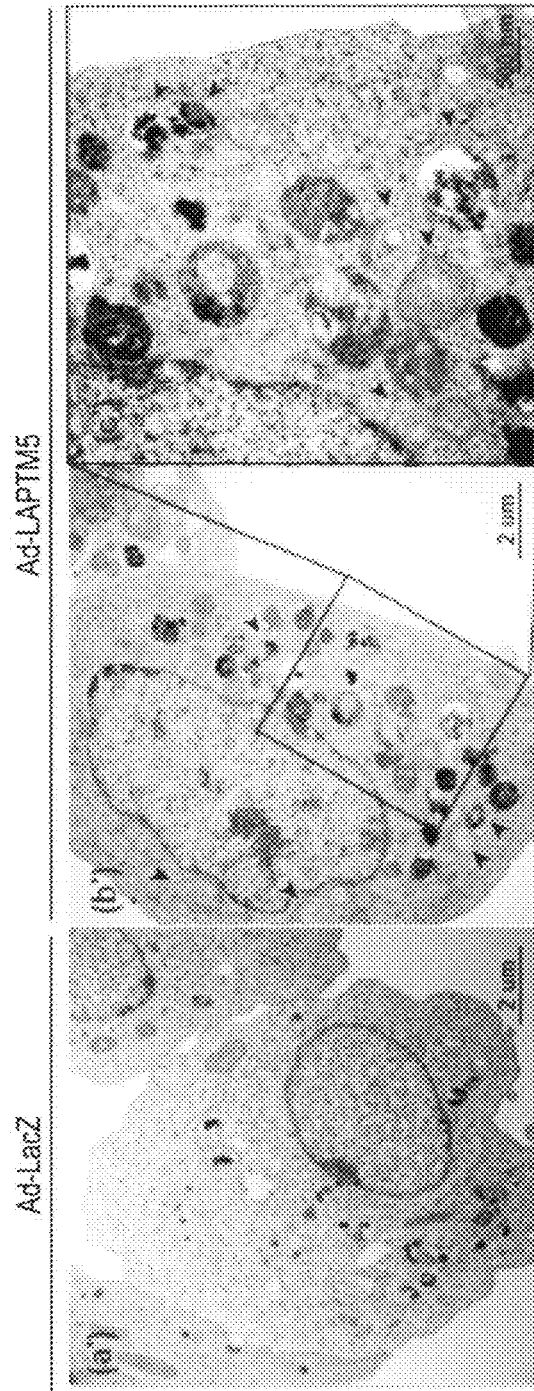
FIG. 2(g) shows images observed under an electron microscope of the GOTO cells infected with Ad-LacZ (left) or Ad-LAPTM5 (center and right). Typical images observed under an electron microscope 4 days after infection are shown. (Right) An image shows an enlarged view of a region enclosed by a rectangle shown in the (center) and shows the number of accumulated autophagic vesicles. An arrow head indicates an autophagic vesicle.

Whether or not LAPTM5-induced cell death was autophagy was then inspected. At the outset, the GFP-LC3 expression vectors were transfected into the neuroblastoma cells (GOTO cells) in order to inspect the pattern of LC3 protein localization in the cytoplasm of the neuroblastoma cells that had died because of LAPTM5-induced cell death, and the cells were cultured in the presence of Geneticin for 3 weeks to establish the cell lines that stably express GFP-LC3. Transfection was carried out using Lipofectamine 2000 (Invitrogen) and experiment was carried out in accordance with the recommended protocol. When cell death was induced via Ad-LAPTM5 infection in the GOTO cells that stably express GFP-LC3, significantly increased dot-like localization of GFP-LC3 was found in the cytoplasm (p=0.003, FIG. 2e), compared with the cells infected with Ad-LacZ. Further, the existence of LC3-II was detected in the GOTO cells that stably express GFP-LC3 infected with Ad-LAPTM5 via Western blot analysis (FIG. 21). Compared with Ad-LacZ-infected cells, the existence of autophagic vesicles was observed in the cytoplasm of substantially all Ad-LAPTM5-infected GOTO cells via electron microscopic analysis (FIG. 2g). Further, some dead cells were found to show necrotic features, such as cytoplasmic vacuolation and a tigroid pattern of a nucleus (FIG. 14).

These results suggest that forced LAPTM5 expression can induce necrosis-like cell death involving the appearance of autophagic vesicles in the neuroblastoma cell lines.

Example 3

Figure 3A:
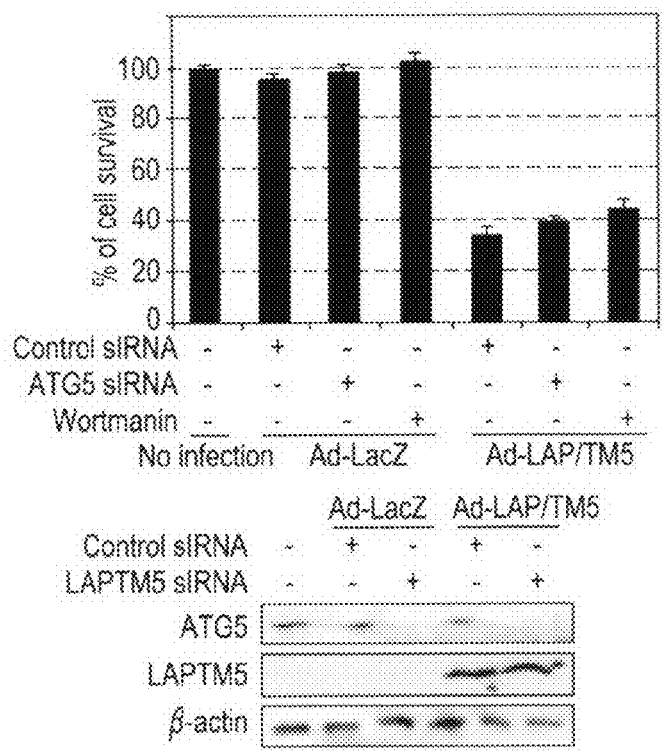
FIG. 3(a) shows influence of the cell survival ratio resulting from ATG5 knock-down and wortmannin treatment upon LAPTM5-induced cell death. ATG5 siRNA or control siRNA was transfected into the GOTO cells ($1 \times 10^4$ cells/well) sowed on a 96-well plate. On the following day, the GOTO cells were infected with 10 MOIs of LacZ (Ad-LacZ) or LAPTM5 (Ad-LAPTM5) adenoviruses. Simultaneously with adenovirus infection, wortmannin treatment was carried out. The percentage of surviving cells was determined via colorimetric assay using a water-soluble tetrazolium salt. A vertical line represents the standard deviation of two experiments. The lower portion shows the results of lowered ATG5 expression caused by ATG5 siRNA confirmed via Western blotting.
Figure 3B:
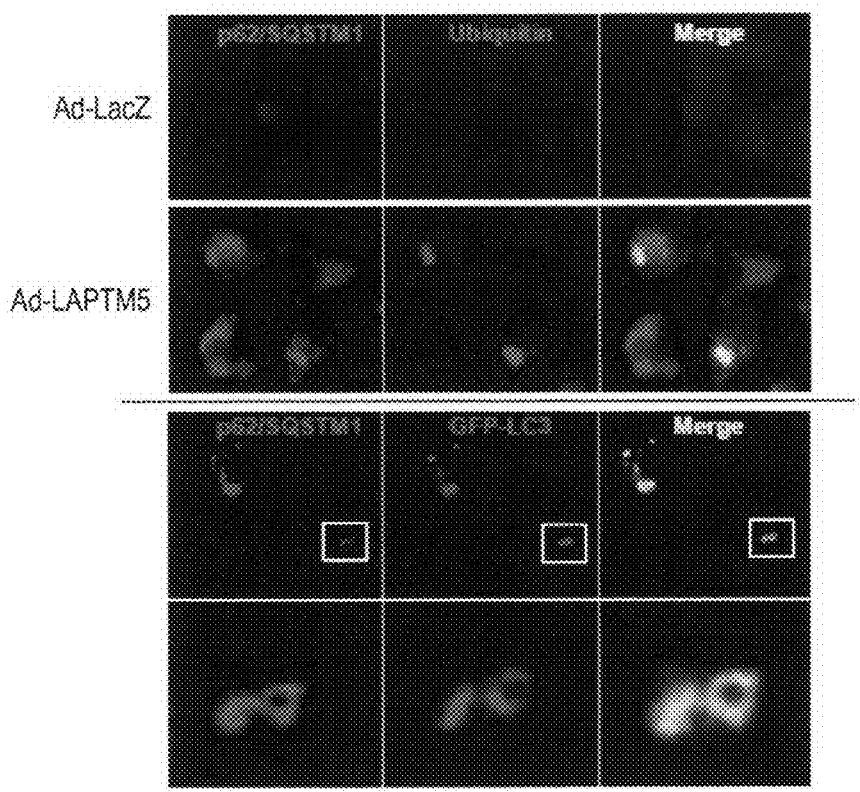
FIG. 3(b) shows expression of p62/SQSTM1 proteins, ubiquitinated proteins, and cathepsin D in the LAPTM5-infected GOTO cells, which was analyzed via Western blotting. The sample shown in FIG. 2b was subjected to SDS-PAGE and Western blot analysis was carried out using relevant antibodies. An arrow represents a form of cathepsin D. An asterisk represents an unknown form. The representative results of two independent experiments are shown.
Figure 3C:
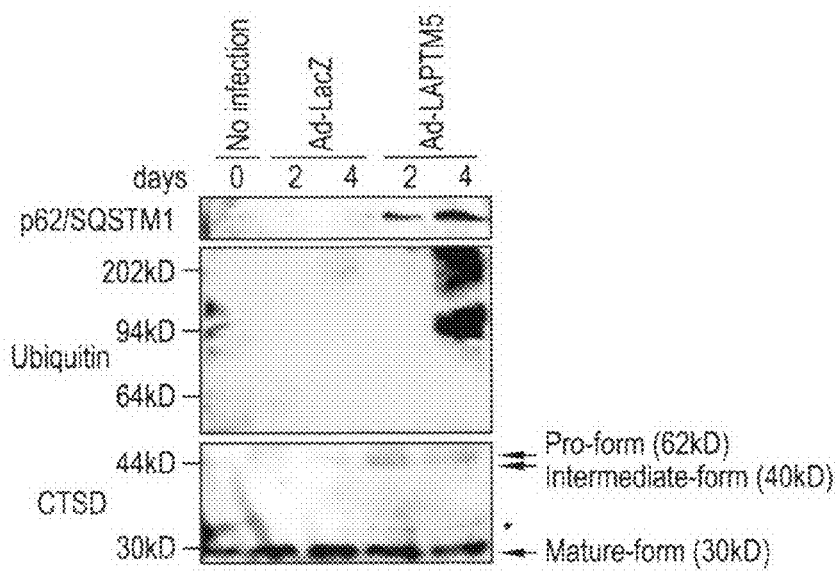
FIG. 3(c) shows accumulation and colocalization of p62/SQSTM1 proteins and ubiquitinated proteins or GFP-LC3 proteins in the LAPTM5-infected GOTO cells, which were elucidated by the immunofluorescence method. The GOTO cells ($5 \times 10^4$ cells/well) were sowed on a 24-well plate and infected with 10 MOIs of Ad-LAPTM5. Four days after infection, the cells were fixed, the reaction was allowed to proceed using the p62/SQSTM1 antibody, and the reaction product was visualized with the use of the Texas-Red secondary antibody. A typical image is shown, wherein DAPI indicates contrast staining.

Induction of Lysosomal Membrane Permeabilization (LMP) and Blocking of Autophagy Pathway in LAPTM5-Induced Cell Death In order to examine the significance of autophagic vesicle appearance in the case of LAPTM5-induced cell death, the effects of suppression of ATG5 gene (the autophagy-associated gene) expression via introduction of a drug (wortmannin) that suppresses autophagic vesicle formation or siRNA were examined (FIG. 3a). As a result, it was demonstrated that LAPTM5-induced cell death would not be suppressed even when autophagy was inhibited. The results suggest that autophagic vesicle appearance in the case of LAPTM5-induced cell death results from accumulation of immature autophagic vesicles instead of autophagy activation. Further, Western blot analysis and fluorescent staining revealed accumulation of p62/SQSTM1 and ubiquitinated proteins that are considered to undergo autophagy-induced proteolysis, when LAPTM5-induced cell death occurred (FIGS. 3b, 3c, and 8). In this case, in some cells that had undergone cell death, p62/SQSTM1 and ubiquitinated proteins were colocalized to form an inclusion corpuscle. As reported in the past, colocalization of p62/SQSTM1 and GFP-LC3 was observed (FIG. 3b). Further, the amount of ubiquitinated proteins was found to increase in fractions that are insoluble in surfactant (Triton-X) via Western blotting. This strongly suggests that ubiquitinated proteins form inclusion corpuscles and are accumulated (FIG. 8b). These results demonstrate that the appearance of autophagic vesicles upon LAPTM5-induced cell death indicates accumulation of immature autophagic vesicles and ubiquitinated proteins caused by blocking of the autophagy pathway.

Figure 3D:
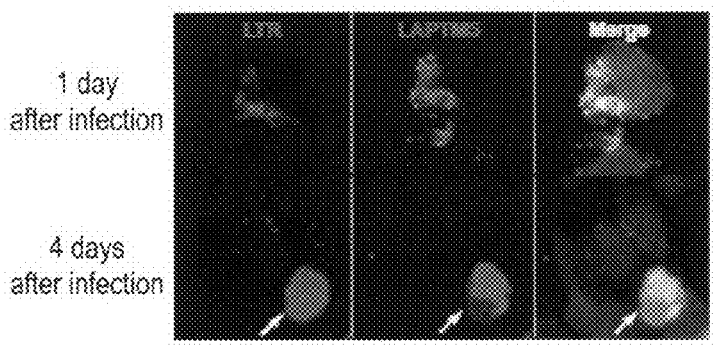
FIG. 3(d) shows a typical image of localization and LysoTracker rhodamine (LTR) staining of LAPTM5 proteins in GOTO cells. The GOTO cells ($1 \times 10^4$ cells/well) were sowed on a 24-well plate and infected with 10 MOIs of adenoviruses (Ad-LAPTM5). One or four days after infection, the cells were stained with LTR, washed twice, and fixed. After the reaction was allowed to proceed with the use of the LAPTM5 antibody, the reaction product was visualized with the use of the FITC complex secondary antibody. DAPI indicates contrast staining. An arrow indicates a cell having the features of LMP.
Figure 3E:
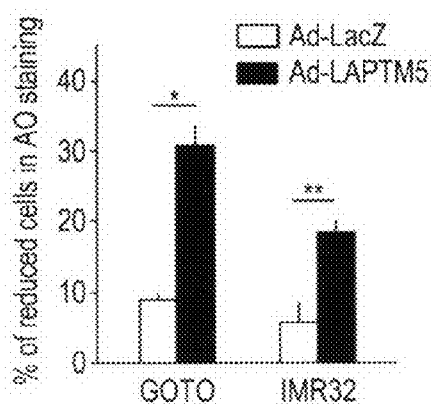
FIG. 3(e) shows acridine orange (AO) staining of the infected GOTO cells and IMR cells. Four days after injection, the infected cells were stained with AO and washed twice with PBS. The staining intensity was measured via flow cytometry in the FL3 channel. The channel opened and closed within a range between cells that are negative for AO fluorescent staining and more than 98% of the infected cells. The radical decrease in AO fluorescence and LAM occurred in the GOTO cells and in the IMR cells in which Ad-LAPTM5 was infected. The lower chart shows the percentage of a decrease in AO fluorescence. A vertical line represents the standard deviation of two independent experiments (*$P<0.01$, **$P<0.05$).
Figure 3F:
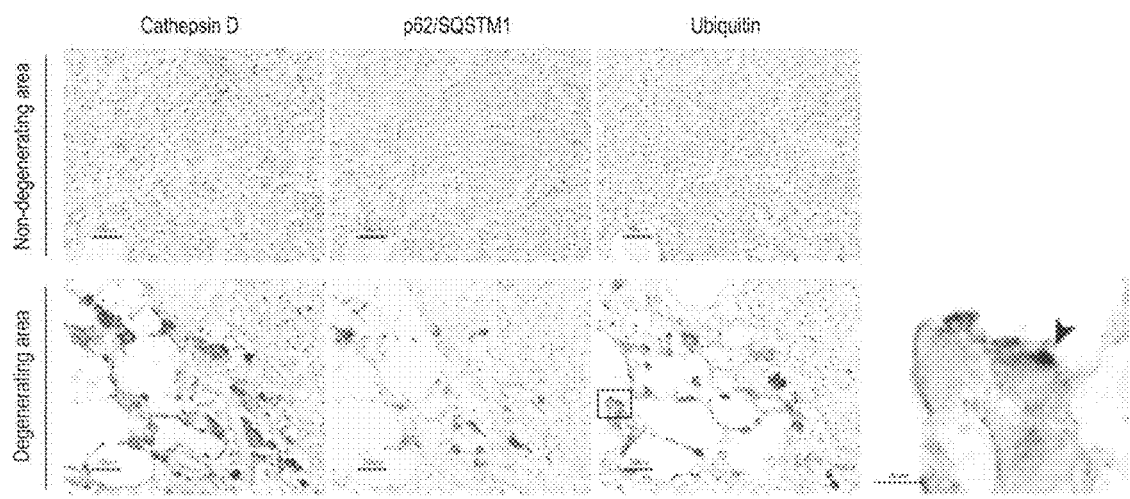
FIG. 3(f) shows immunohistological staining with the use of antibodies reacting with cathepsin D, p62/SQSTM1, and ubiquitinated proteins. A continuous section was subjected to the reaction with each antibody. The upper portion shows a stained image of the non-degenerating site and the lower portion shows a representative stained image at the degenerating site.

LAPTM5 is known to be a membrane protein that localizes in the lysosome. LAPTM5 that is actually forced to express 1 day after adenovirus infection shows dot-like colocalization with the LysoTracker rhodamine (LTR), which is a lysosomotropic fluorescent probe (FIG. 3d). In correlation with LAPTM5 accumulation, however, dot-like staining patterns of LTR were found to often disappear 4 days after infection (FIG. 3d). Such changes in LTR staining patterns result from LMP, which indicates destabilization and destruction of the lysosome. LMP was observed along with an increase in LAPTM5-induced cell death (2.7 times in GOTO cell (p=0.0007) and 5.4 times in IMR32 cell (p=0.0108), compared with Ad-LacZ cell; FIG. 11). Further, another LMP marker; i.e., acridine orange (AO) stain, was found to decrease along with LAPTM5-induced cell death (FIGS. 3e and 11). In some dead cells, release of hydrolase cathepsin D (CTSD) from the lysosome to the cytoplasmic sol and increased intermediate forms were observed (FIGS. 3c, 3d, and 11). These results suggest that forced LAPTM5 expression induces lysosomal cell death involving destabilization and destruction of the lysosome mediated by LMP. Accordingly, LAPTM5-induced LMP was deduced to induce blocking of the autophagy pathway. In fact, when treatment with an LMP inducer; i.e., ciprofloxacin (CPX) (LKT laboratories), is performed in the GOTO cells that stably express GFP-LC3, LC3-II was detected and p62/SQSTM1 protein accumulation was observed as in the case of LAPTM5-induced lysosomal cell death (FIG. 12). In conformity with the results of in vitro observation, elevated expression of p62/SQSTM1, ubiquitinated proteins, and cathepsin D was also observed via immunohistological staining (FIG. 3f). Also, formation of ubiquitin-positive inclusion corpuscle was observed in some cells. The results suggest that LAPTM5 expression induces lysosomal cell death involving destabilization of the lysosome mediated by LMP. At the same time, lysosome instability induced by LAPTM5 was considered to induce accumulation of immature autophagic vesicles and ubiquitinated proteins.

Example 4

Figure 4A:
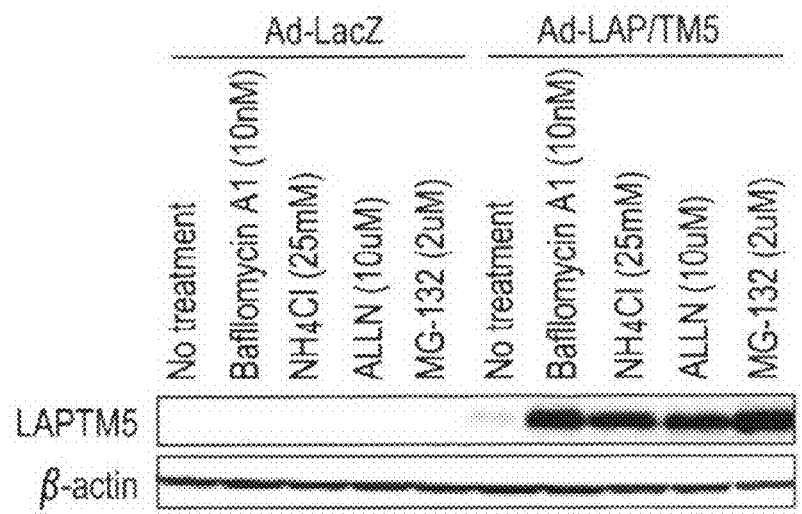
FIG. 4(a) shows the GOTO cells ($5 \times 10^4$ cells/well) were sowed on a 24-well plate and infected with Ad-LacZ or Ad-LAPTM5. The cells were treated with a proteasome inhibitor (ALLN or MG132) or a lysosomal degradation inhibitor (Bafilimycin A1 or ALLN) 1 day later. The cells were recovered 1 day later, the samples were prepared, and Western blot analysis was then carried out. The prepared samples were subjected to SDS-PAGE, and Western blot analysis was carried out using relevant antibodies.
Figure 4B:
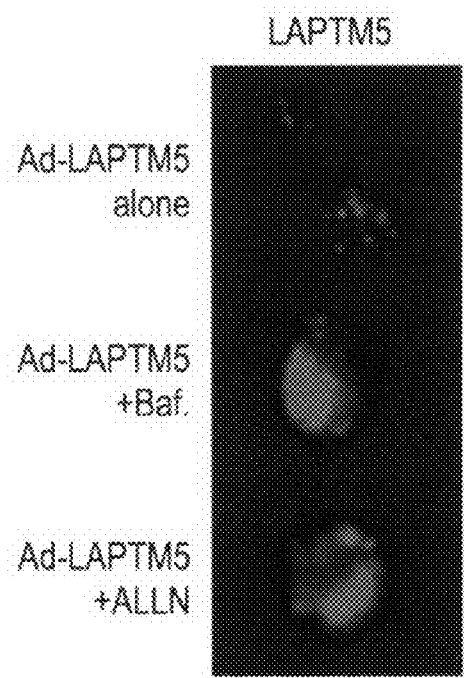
FIG. 4(b) shows LAPTM5 accumulation observed via fluorescent immunostaining. As with the case of (a), the cells were treated, fixed, subjected to the immune reaction using the LAPTM5 antibody, and visualized with the use of the Texas Red complex secondary antibody.
Figure 4C:
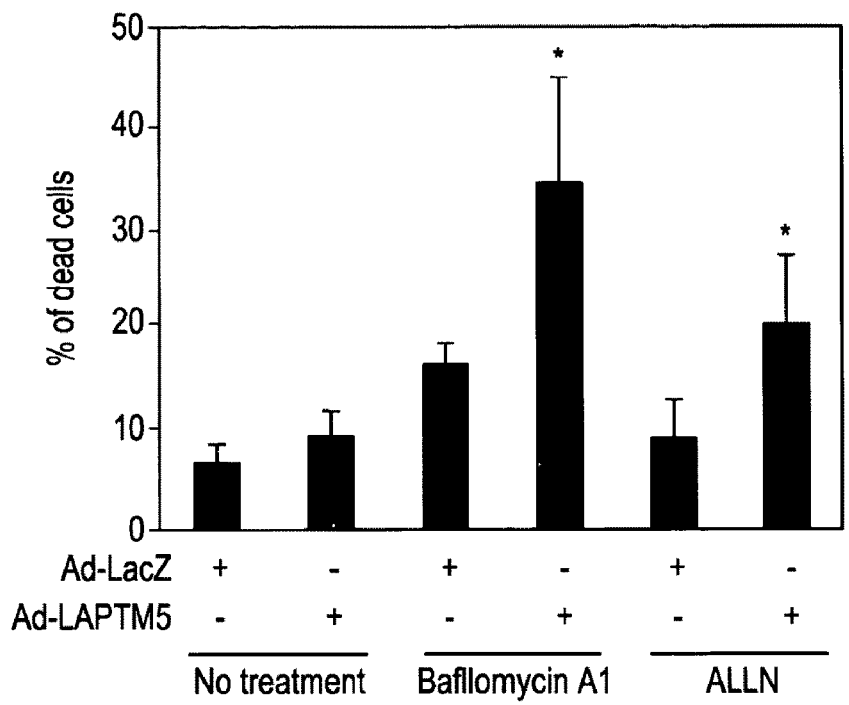
FIG. 4(c) shows an increase in frequency of cell death along with LAPTM5 accumulation. As in the case of (a), the cells that had died upon treatment were assayed via trypan blue exclusion. A vertical line represents the standard deviation of two experiments.
Figure 4D:
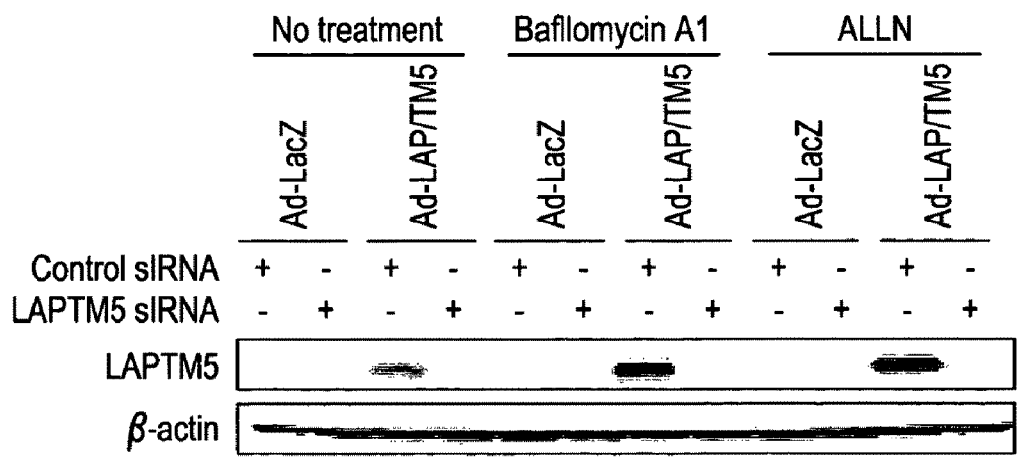
FIG. 4(d) shows suppression of LAPTM5 expression via treatment with siRNA of LAPTM5. After the control or LAPTM5 siRNA was transfected, the cells were treated as with the case of (a), and the samples were prepared. Western blot analysis was carried out using the LAPTM5 antibody.
Figure 4E:
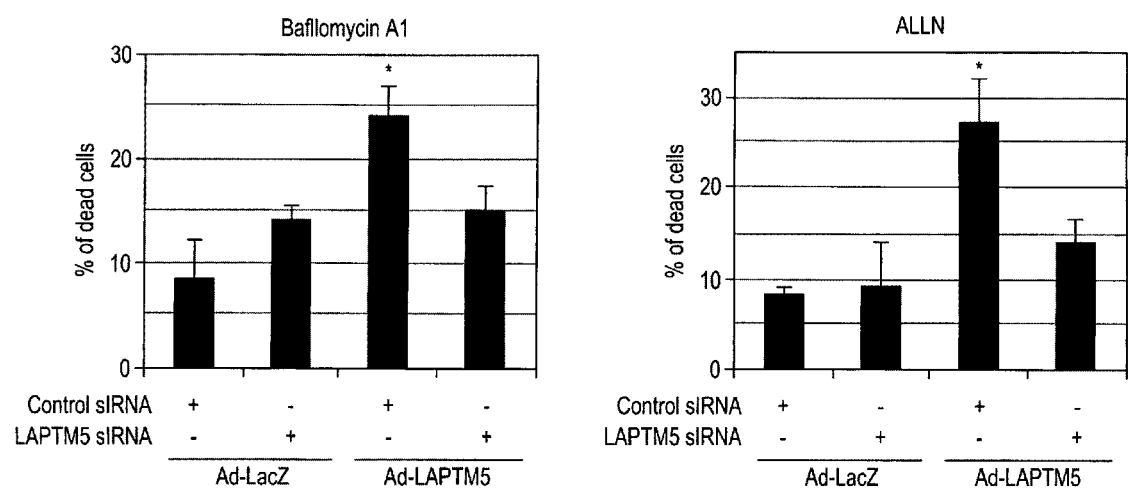
FIG. 4 shows LAPTM5 accumulation and induction of cell death by blocking the proteasomal or lysosomal degradation pathway.

LAPTM5 Accumulation and Induction of Cell Death by Blocking Proteasomal or Lysosomal Degradation Pathway In the GOTO cells, LAPTM5 that had been forced to express by adenovirus was observed to be accumulated. Accordingly, whether or not LAPTM5 would undergo proteasomal or lysosomal proteolysis and whether or not LAPTM5 accumulation would be important for cell death were inspected. One day after Ad-LAPTM5 infection, the cells were treated with a proteasome inhibitor (ALLN or MG132) or a lysosome inhibitor (Bailomycin A1 and NH4Cl) for additional one day. Thereafter, the cells were recovered, samples were prepared, and Western blot analysis was performed. As a result, expressed LAPTM5 was found to be significantly accumulated via treatment with a proteolysis inhibitor (FIG. 4a). Further, this accumulation was also confirmed via fluorescent staining using the LAPTM5 antibody (FIG. 4b). Also, cell death frequency significantly increased along with LAPTM5 accumulation (FIG. 4c). Thus, LAPTM5 was considered to undergo proteasomal and lysosomal proteolysis, and LAPTM5 accumulation was considered to be deeply involved with induction of cell death. In order to examine whether or not LAPTM5 accumulation would be essential for induction of cell death, the influence of transfection of siRNA against LAPTM5 was then examined. As a result, it was confirmed by Western blot analysis that LAPTM5 accumulation caused by treatment with Bafilomycin A1 or ALLN was significantly suppressed in cells in which siRNA against LAPTM5 had been transfected (FIG. 4d). In this case, frequency of cell death caused by LAPTM5 accumulation was found to be significantly lowered (FIG. 4e). This indicates that LAPTM5 accumulation is deeply involved in induction of cell death and that suppression of LAPTM5 expression is capable of suppression of cell death.

Example 5

Figure 5A:
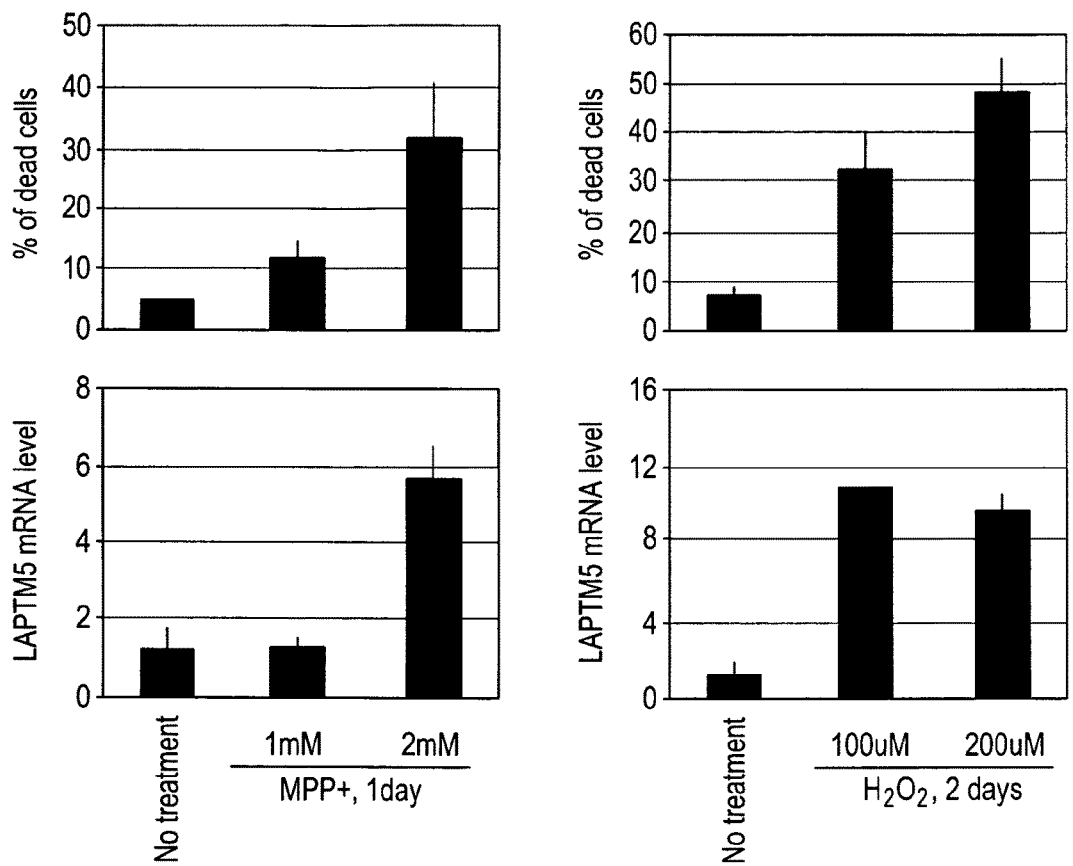
In FIG. 5(a), the GOTO cells were treated with MPP+ (1 or 2 mM) for 24 hours or with $H_2O_2$ (100 or 200 uM) for 48 hours. Thereafter, the dead cells were assayed via trypan blue exclusion. The LAPTM5 expression level was analyzed via quantitative RT-PCR. A vertical line represents the standard deviation of two experiments.
Figure 5B:
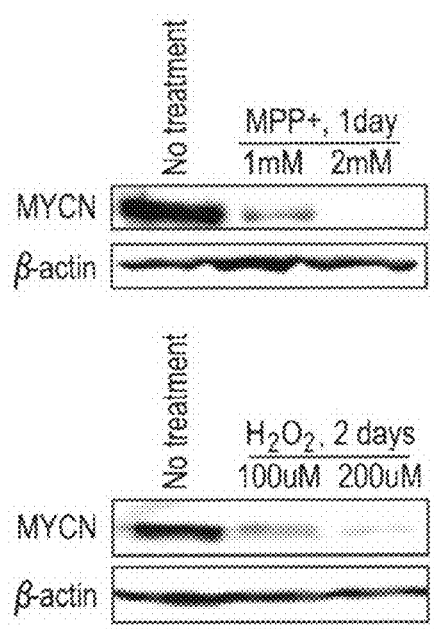
FIG. 5(b) shows the MYCN expression level which was analyzed via Western blot analysis. The prepared samples were subjected to SDS-PAGE, and Western blot analysis was carried out using relevant antibodies.
Figure 5C:
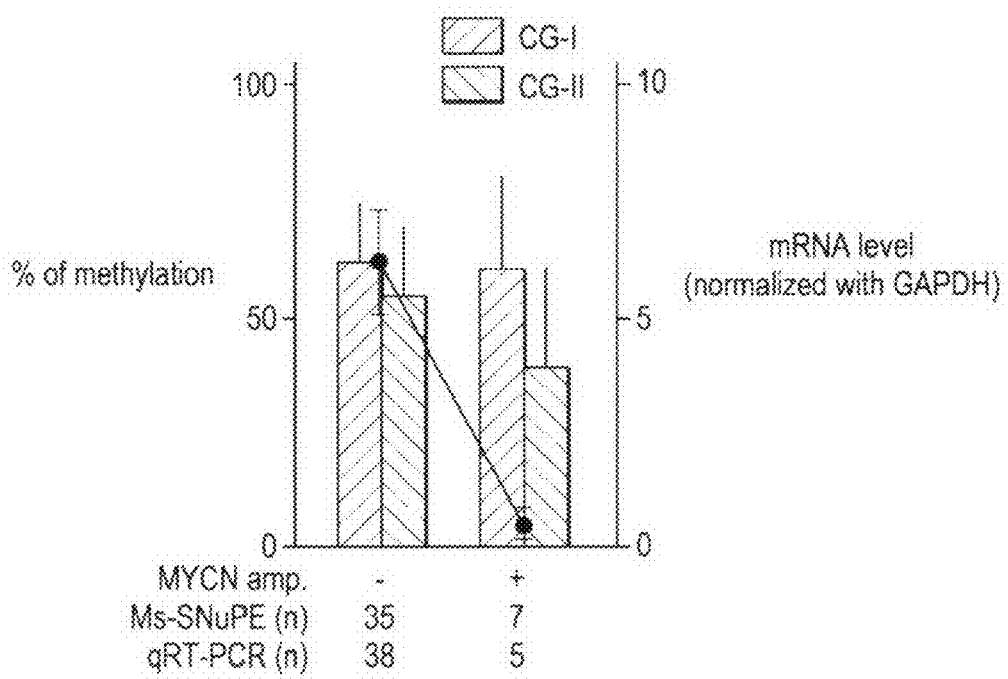
FIG. 5(c) shows comparison of methylation frequency and expression level of LAPTM5 in MYCN-amplified tumor specimens and in non-amplified specimens. The mRNA level of LAPTM5 was assayed via real-time quantitative RT-PCR and was shown with a dot. Methylation frequencies at 2 CG sites (CG-I or CG-II) were assayed via Ms-SNuPE and were shown with a dark gray (CG-I) or light gray (CG-II) bar. "n" indicates the number of specimens. A vertical line represents the standard deviation.
Figure 5D:
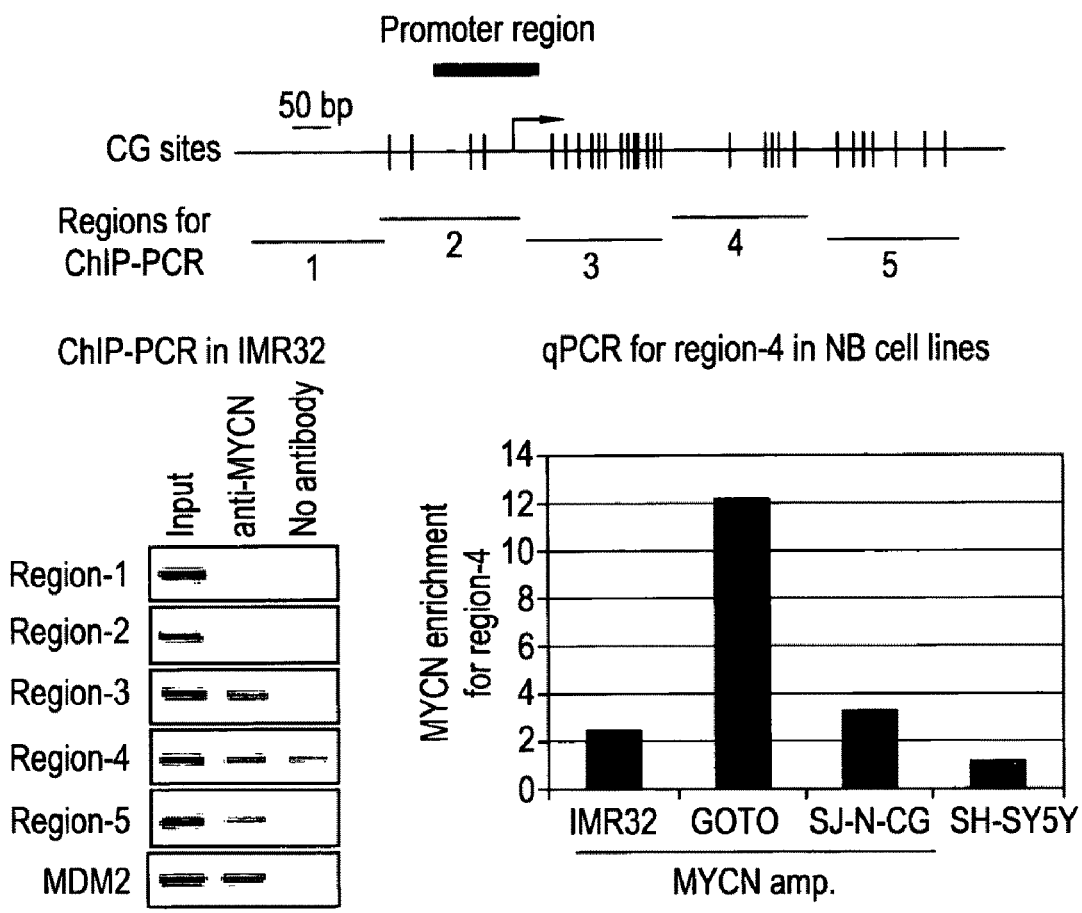
FIG. 5(d) shows the results of the chromatin immunoprecipitation method (CUP assay) using the MYCN antibody. The upper portion indicates a map showing the vicinity of the transcription initiation point of the LAPTM5 gene and the positions of 5 types of primers. The lower left portion shows the results of ChIP-PCR of the IMR32 cells. PCR was carried out using the respective primers and MDM2 gene primers, and the PCR product was separated on agarose gel. The lower right portion shows the results of ChIP-PCR of the region 4 in the neuroblastoma cell line. ChIP-PCR of the MYCN-amplified IMR32, GOTO, and SJ-N-CG cells and the non-amplified SH-SY5Y cells was carried out via quantitative PCR. The chart shows a relative value obtained by the formula: MYCN enrichment=(MYCN-ChIP value−IgG-ChIP value)/input value while designating the value of SH-SY5Y cell as 1.0.
Figure 5E:
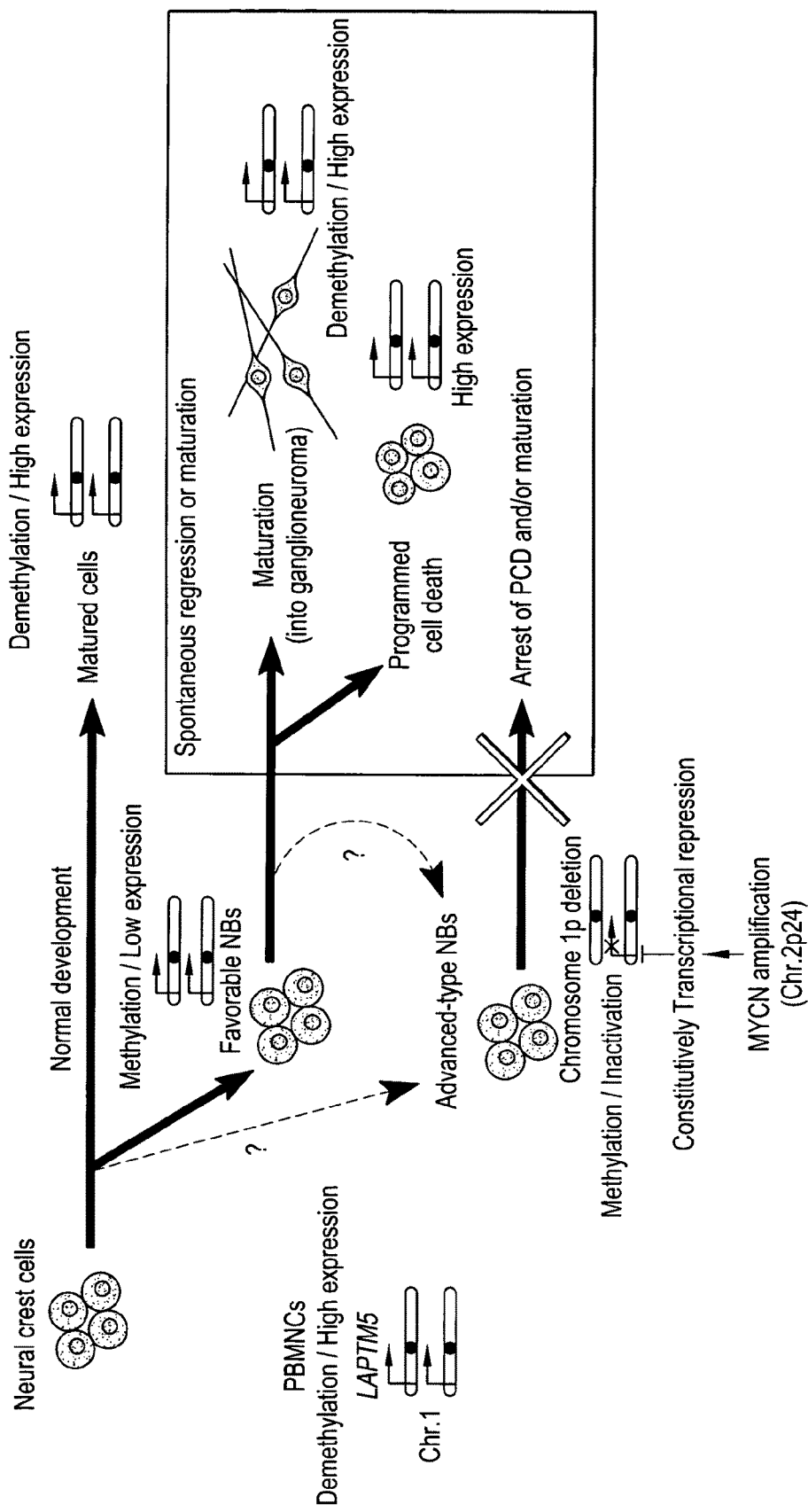
FIG. 5(e) shows the model regarding biological significance of LAPTM5 inactivation in unfavorable neuroblastoma

LAPTM5 Activation by Mitochondrial Injury or Oxidative Stress and Transcription Suppression by MYCN The cause for NB cell degeneration upon regression of favorable NB tumors has not yet been elucidated. As shown in FIG. 3, ubiquitin-positive inclusion corpuscles that are observed in neurodegenerative diseases such as Parkinson's disease were also observed in LAPTM5-associated degenerating cells both in vivo and in vitro. This indicates a common mechanism between NB tumor regression and cell degeneration in the case of neurodegenerative diseases. Mitochondrial injury and oxidative stress are known to be deeply involved in neuron degeneration in the case of neurodegenerative disease. Thus, whether or not such stress is involved in activation of LAPTM5 expression in the NB cell line was examined. When the GOTO cells were treated with mitochondrial injury-inducing MPP+ (1-methyl-4-phenylpridinium) or a type of oxidative stress ($H_2O_2$), LAPTM5 expression was found to be activated as the frequency of concentration-dependent cell death increased (FIG. 5a). MYCN expression was found to decrease along with the treatment (FIG. 5b). Further, the mRNA level of LAPTM5 in unfavorable NB tumor specimens with MYCN gene amplification was found to be lower than that of the specimens having no such gene amplification, regardless of the methylation frequency (P=0.0005) (FIG. 5c). MYCN proteins are known to not only activate but also suppress transcription of various target genes. Accordingly, MYCN proteins that have been activated via amplification were considered to suppress activation of LAPTM5 transcription induced by stress. Thus, whether or not MYCN would directly bind to a site in the vicinity of the transcription initiation point of the LAPTM5 gene was inspected via ChIP assay. As a result, MYCN was found to bind to a region containing a candidate MYCN-binding sequence in intron 1 of the LAPTM5 gene (FIG. 5d). Meanwhile, the IMR32 cell line is known to differentiate into nerve cells via treatment with retinoic acid. In this case, activation of LAPTM5 expression and suppression of MYCN expression were observed (FIG. 13).

The above results suggest a possibility such that, in addition to a mitochondrial injury or oxidative stress, a stimulus of differentiation induction is deeply involved in activation of LAPTM5 expression, and MYCN directly suppresses an increase in LAPTM5 expression. Accordingly, it is deduced that LAPTM5 is constantly inactivated in unfavorable NB specimens via suppression of expression by LAPTM5 deletion and MYCN amplification and that the capacity for cell growth is maintained.

TABLE 1

List of BACs containing possibly methylated regions in NB cell lines compared to control stage1 NB tumors or PBMNCs by BAMCA analysis

| | | | BAMCA ratio[b] | | | | | | Down-regulation | Differentially | Methylation |
| | Chr. band | | GOTO | | IMR32 | | | | of expression in | methylated | status in NB |
| BACs | (distance:cM)[a] | STS | 1 | 2 | 1 | 2 | Genbank No. | Symbol | both cell lines[c] | SmaI sites[d] | tumors[e] |
|---|---|---|---|---|---|---|---|---|---|---|---|
| | | | | NB stage1 vs. NB cell line | | | | | | | |
| 127J4 | 1p36.2 (16.5) | D1S1309 | 2.56 | 2.49 | 2.34 | 2.22 | NM_018090 | FLJ10420 | no | — | — |
| | | | | | | | XM_057040 | KIAA1922 | yes | no | — |
| 31GC6 | 1p36.1 (21.8) | stSG9189 | 1.34 | 1.18 | 1.78 | 1.78 | NM_032236 | USP48 | no | — | — |
| | | | | | | | NM_002885 | RAP1GA1 | yes | yes | Unmethylated |
| | | | | PBMNCs vs. NB cell line | | | | | | | |
| 418B22 | 1p35.1 (30) | D1S1348 | 1.58 | 1.57 | 1.22 | 1.10 | NM_002379 | MANT1 | no | no | — |
| | | | | | | | NM_008762 | LAPTM5 | yes | yes | Methylated |

[a]Distance from the top of short arm on chromosome 1
[b]BAMCA ratios were indicated by resulting for duplicate spots (1 and 2)
[c]The presence ('yes') or absence ('no') of expression for each genes was determined by RT-PCR as indicated in FIG. 1B
[d]The presence ('yes') or absence ('no') of differential methylation in SmaI sites for each gene was determined by MS-PCR as indicated in FIG. 6C. '—' indicates 'not tested'.
[e]The methylation status of RAP1GA1 and LAPTM5 in primary NB tumors was determined by COBRA as indicated in FIG. 6B. '—' indicates 'not tested'.

TABLE 2

(SEQ ID NOS: 1-75)
Primer sequences

| Applications | Forward (5'-3') | Reverse (5'-3') |
|---|---|---|
| Methylation analysys | | |
| Bisulfite sequencing & COBRA | | |
| LAPTM5-region-I | TGGTAGTGTTTTTTTAGTAAGT | AAAAATTCTTTCATTTATAAAAA |
| LAPTM5-region-II | GTTAAATGGTTGGGGGTATTTTG | AACTTCACAAATTACCCAACAA |
| RAP1GA1 | TTAGTTGTTGTTAAGAT | AAAACCCTCCTCCAAAACCTA |

TABLE 2-continued (SEQ ID NOS: 1-75)
Primer sequences

| Applications | Forward (5'-3') | Reverse (5'-3') |
|---|---|---|
| MS-SNuPE | | |
| Primer for extension (19 mer) | TGTTTC/TGTTTTAGTTGTGA | |
| MS-PCR | | |
| SmaI-1 | TTAACCACAGGCCCCTGAGTC | GCTTCCAGCTCAGTCAAACC |
| SmaI-2 | CAGAGAGGTGGAGAGCAGGA | CCCCTTCAGTGTCTCAGAGG |
| No. 1 | TAGCAAAGGGTCCTGAAGTT | GCTCACTGCAAGCTCCGCCT |
| No. 2 | AGACAGACGGGGCCCCCTT | CCACACATCATATGCAGGTG |
| No. 3 | CCTCCAGTGAGATGTGCATT | TGCCTGGGGTGTCCTTTCAC |
| No. 4 | TGGCTTCTCTCCTCCATCCT | GACCCCTGGCTGCCTCTTTC |
| No. 5 | GCCACCAGGGGCTCACTTGG | AGACGTCTGGCTGGCCAGGC |
| No. 6 | ACACACCAAAGCCTGCCTGG | GGTGCAGTGAGCGATGAGCC |
| No. 7 | CCAGACACACCCCCTCCCACC | TCCCTTAAGCCCCTCACCTC |
| No. 8 | CAGGGCCAGGACTCAGGATT | CTGTGTCCAGTGGGGCTAGG |
| No. 9 | ACAATGCCCACCTTCTGGGC | CGCCAGGAAAACGGCGTGAA |
| No. 10 | GCTCACTGCAAGCTCCGCTT | GCAGGACGTGTCTGCGCGGG |
| No. 11 | GGTCGCACAGCCAGGCGGCA | ACCCAGCCCCGGCCGGGCCT |
| No. 12 | AACCTTAACAGCCCCACAGT | CAGATGGGGCCTGCGGTGAC |
| No. 13 | GGGTGGGCCAAGCAAGGGCT | GTCTTGGGCAAGTCACAGTG |
| No. 14 | GCAGAGGGGCAGCCTTGGCC | CCATGTGGTGAGTGTGCGGG |
| No. 15 | CAAGAGGCCCAGGACACCAT | TGGTGTTGCAGCCCGGAACC |
| No. 16 | GCTCACTGCAAGCTCCACCT | GGGCTTGAGATCCCGAGAGG |

Expression analysis

| | | |
|---|---|---|
| Quantitative RT-PCR | | |
| LAPTM5 | GTCCCTGCAAATGATGGACT | AGGTGGGCACTTCCATGTAG |
| TaqMan Probe | 6-CCGTGCTAGCTCCTCCAAGTTCC-TAMRA | |
| Standard RT-PCR | | |
| RAP1GA1 | CTACCGGAAGCACTTTCTCG | CACACACCAACTTTGCCATC |
| USP48 | AACTCATTTGTGGGCCTGAC | TTGAGCATCCTGCTGTTGTC |
| FLJ10420 | TTCAGGCAGCAGTGTTCATC | TAAACCAAGCAACCCTGGAC |
| KIAA1922 | AAGCACAATCACCTGCTCCT | GTCCGTGTTGACCTGATCCT |
| LAPTM5 | GTCCCTGCAAATCATGGACT | AGGTGGGCACTTCCATGTAG |
| MATN1 | ATCGAGAAGCTGTCCAGGAA | GGATCCGTCAATGAGGAAGA |
| ChIP assay | | |
| region-1 | CCTCAGTTTCTTCATCTGTA | CCAGGACTGTTACCAAGCCC |
| region-2 | CTTCCAAAGTTGGTAGTGTT | CCTGCCCCTTAGACAGGCAG |
| region-3 | AAGGAAGTGAGGAGGGCAGC | TTCAGACTCACACAAGCACG |
| region-4 | TGTCTGCGGTGACCCGTCAT | ACAGAGGCAGAAACGGAGCC |
| region-5 | GTGAGGTCGGCCGCAGACAC | CCAGTGACAGCCGTGACTTC |
| MDM2 | AGCCTTTGTGCGGTTCGTG | CCCCCGTGACCTTTACCCTG |
| Construction Expression vector | | |
| GFP-LAPTM5 XhoI/EcoRI | CCGCTCGAGATGGACCCCCGGTTGTC | CCGGAATTCTCACACCTCTGAGTAT |
| pAxCAwt/t-LAPTM5 | ATGGACCCCCGCTTGTCCAC | TCACACCTCTGAGTATGGG |

TABLE 3

Relationship of LAPTM5-associated degeneration with patient and tumor characteristics

|  | INSS stage | Cases | Positive (%)[a] | P[b] |
|---|---|---|---|---|
| Mass screened NB | 1 | 25 | 22 | |
|  | 2 | 17 | 13 | |
|  | 3 | 6 | 5 | |
|  | 3 (MYCN amp.) | 1 | 0 | |
|  | 4 | 0 | 0 | |
|  | 4 (MYCN amp.) | 1 | 0 | |
|  | 4S | 4 | 2 | |
| Total |  | 54 | 42 (77.8%) | |
| Clinically detected NB | 2 | 1 | 1 | |
|  | 3 | 1 | 0 | |
|  | 4 | 4 | 0 | |
|  | 4 (MYCN amp.) | 11 | 0 | |
| Total |  | 17 | 1 (5.9%) | <0.000001 |

[a] the number indicate a number of NB tumors with LAPTM5-positive degeneration
[b] Comparison was made of the proportions of positive cases between mass screened NB and clinically detected NB, and the difference was tested by $X^2$-test.
NB; neuroblastoma, INSS; International Neuroblastoma Staging System

TABLE 4

Summary of copy-number aberrations for MYCN, LAPTM5, and 1p35 region in 10 NB cell lines

| | | Copy-number aberrations (by array CGH & CGH analysis)[a] | | Copy-number (by FISH analysis)[b] | |
|---|---|---|---|---|---|
| No. | cell line | MYCN amplification | 1p35 loss | 418B22 (LAPTM5) | pUC1.77 |
| 1 | GOTO | yes | yes | 1 | 3 |
| 2 | IMR22 | yes | yes | 3 | 5 |
| 3 | SJ-N-CG | yes | no | 1 | 6 |
| 4 | CHP134 | yes | no | 3 | 2 |
| 5 | MP-N-MS | yes | yes | 1 | 2 |
| 6 | KP-N-RT | yes | yes | 1 | 2 |
| 7 | SK-N-AS | no | no | 2 | 3 |
| 8 | SH-SY5Y | no | no | 2 | 2 |
| 9 | SK-N-SH | no | no | 2 | 3 |
| 10 | SJ-N-KP | no | no | 2 | 3 |

[a] Copy-number status for MYCN gene locus and 1p35 region was determined by array-CGH and coventional CGH analysis. "yes" indicates the presence of MYCN amplification or 1p35 loss, and "no" indicated the absence of them.
[b] Two probes were used for FISH analysis. 418B22 (BAC clone), spotted on 1p36-contig array is mapped on 1p35 and contain LAPTM5 gene locus. The pUC1.77 (plasmid) as a control is mapped on the pericentromeric region of chromosome 1.

The invention claimed is:

1. A method for detecting neuroblastoma which comprises detecting inactivation of the lysosomal-associated protein multispanning transmembrane 5 (LAPTM5) gene and amplification of the MYCN gene in a neural crest-derived tissue from a subject,
wherein inactivation of the LAPTM5 gene and amplification of the MYCN gene in the neural crest-derived tissue from the subject indicates the subject has a neuroblastoma.

2. The method for detecting neuroblastoma according to claim 1, wherein inactivation of the LAPTM5 gene is caused by methylation at the CpG site in the vicinity of the transcription initiation point, deletion of the LAPTM5 gene, or suppression of transcription by MYCN.

3. A method for detecting neuroblastoma according to claim 1, wherein the inactivation of the lysosomal-associated protein multispanning transmembrane 5 (LAPTM5) gene is detected by detecting the amount of proteins translated from the lysosomal-associated protein multispanning transmembrane 5 (LAPTM5) gene.

4. The method for detecting neuroblastoma according to claim 3, wherein the amount of proteins translated from LAPTM5 gene is detected by an immunohistochemical method.

* * * * *